(12) United States Patent
Peterson et al.

(10) Patent No.: US 11,427,860 B2
(45) Date of Patent: Aug. 30, 2022

(54) IDENTIFICATION OF SELECTED SPECTRUM ANTIBIOTICS

(71) Applicant: TRANA DISCOVERY, INC., Cary, NC (US)

(72) Inventors: Steven E. Peterson, Cary, NC (US); Samuel P. Yenne, Raleigh, NC (US); Joseph Christopher Ellis, Westfield, IN (US); Richard H. Guenther, Cary, NC (US)

(73) Assignee: TRANA DISCOVERY, INC., Cary, NC (US)

( * ) Notice: Subject to any disclaimer, the term of this patent is extended or adjusted under 35 U.S.C. 154(b) by 14 days.

(21) Appl. No.: 15/751,441

(22) PCT Filed: Aug. 11, 2016

(86) PCT No.: PCT/US2016/046567
§ 371 (c)(1),
(2) Date: Feb. 8, 2018

(87) PCT Pub. No.: WO2017/027713
PCT Pub. Date: Feb. 16, 2017

(65) Prior Publication Data
US 2019/0024152 A1 Jan. 24, 2019

Related U.S. Application Data

(60) Provisional application No. 62/204,173, filed on Aug. 12, 2015.

(51) Int. Cl.
*C12Q 1/6837* (2018.01)
*C12N 15/115* (2010.01)
*C12Q 1/18* (2006.01)
*C12N 15/11* (2006.01)

(52) U.S. Cl.
CPC ............ *C12Q 1/6837* (2013.01); *C12N 15/11* (2013.01); *C12N 15/115* (2013.01); *C12Q 1/18* (2013.01); *C12N 2310/3517* (2013.01); *C12N 2320/12* (2013.01); *C12N 2503/02* (2013.01)

(58) Field of Classification Search
None
See application file for complete search history.

(56) References Cited

U.S. PATENT DOCUMENTS

| 6,300,318 B1 | 10/2001 | Nielsen | |
|---|---|---|---|
| 2010/0069260 A1* | 3/2010 | Guenther | C12Q 1/68 506/16 |

FOREIGN PATENT DOCUMENTS

| RU | 2486251 C2 | 6/2013 |
| WO | 2008/064304 A2 | 5/2008 |
| WO | 2010/036795 A2 | 4/2010 |

OTHER PUBLICATIONS

Gao et al FEBS Letters. 2010. 584: 99-105 (Year: 2010).*
Wikipedia definition for "Base pair." Available via URL: <en.wikipedia.org/wiki/Base_pair>, printed on Mar. 1, 2021 (Year: 2021).*
Kothe et al Molecular Cell. 2007. 25: 167-174 (Year: 2007).*

* cited by examiner

*Primary Examiner* — Carla J Myers
(74) *Attorney, Agent, or Firm* — David S. Bradin; Nexsen Pruet, PLLC

(57) ABSTRACT

Methods are disclosed for identifying antibacterial compounds which inhibit propagation of selected spectrum bacteria, which bacteria use specific tRNA to code for Ala, Met, Ser, or Leu that other bacteria do not use. In one embodiment, the selected spectrum bacteria use GCA to code for Ala, whereas other bacteria use a different codon to code for alanine. The methods involve determining whether putative inhibitors promote or inhibit complex formation between the tRNA and a bacterial ribosome, or between the tRNA and an aminoacyl synthetase. Compounds which promote or inhibit complex formation can disrupt protein production, which bacteria need to propagate. The identified antibacterial compounds can selectively inhibit bacterial propagation. By limiting their effects to the selected spectrum bacteria, these compounds can treat or prevent specific bacterial infections without disrupting the normal bacterial flora, the patients' microbiome, or causing antibacterial resistance.

10 Claims, 6 Drawing Sheets
Specification includes a Sequence Listing.

```
                    *Fluorescein
           C    G
           C    GU   A
           G    C
           C    G
        U        C

U              A cmo5U GC

SEQ ID. No. 15
```

FIG. 4A

```
                    *Fluorescein
           A    U
           U    A
           G    C
           G    C
           C    G
        s2C        A U              t6A mnm5U C U SEQ ID No. 16
```

FIG. 4B

IDENTIFICATION OF SELECTED SPECTRUM ANTIBIOTICS

CROSS-REFERENCE TO RELATED APPLICATIONS

The present application is a National Stage Application under 35 U.S.C 371 of PCT/US2016/046567, filed Aug. 11, 2016, which claims priority to U.S. Provisional Application No. 62/204,173, filed Aug. 12, 2015, the contents of each of which are incorporated herein for all purposes.

FIELD OF THE INVENTION

The present invention concerns antibacterial agents that are directed against tRNA targets, particularly, targets specific for certain Gram negative bacteria, such as *Pseudomonas aeruginosa* LESB58, *Klebsiella pneumoniae* 342, *Escherichia coli* O157 H7 EC4115, and *Acinetobacter baumannii* AYE, and a few Gram positive bacteria, and methods of screening for antibacterial and agents directed against such tRNA targets.

BACKGROUND OF THE INVENTION

The need to discover new classes of antibiotic compounds and/or antibiotics with different target sites is being reiterated frequently with the threat of drug resistant pathogens, reemerging pathogens and/or bio-terrorism concerns. With each passing decade, strains of virtually all important bacterial pathogens of humans have arisen that are resistant to at least one class of antibiotics, and strains resistant to multiple classes of antibiotics have become increasingly widespread. In fact, according to the Centers for Disease Control and Prevention (CDC 2000-2001), virtually all significant bacterial infections in the world are becoming resistant to the antibiotic treatment of choice. This rise is generally attributed to pathogens which have become resistant to commonly used antibiotics which focus on a limited number of target sites. Some pathogens that were generally considered historical disease causing agents are reemerging either due to genetic modifications making the organism more virulent and/or exposure to a larger portion of the world population. Related to the naturally occurring genetic modifications are intentional genetic modifications conducted by groups with bio-terrorist desires. Frequently, these intentional genetic modifications will focus on making an otherwise susceptible disease pathogen resistant to the current antibiotics with known target sites.

For Gram negative bacteria in particular, evolving resistance mechanisms have created significant treatment challenges over the years. In June, 2014, the CDC issued a warning that in hospitalized patients, carbapenem-resistant Enterobacteriaceae (CRE) were a real threat. Some CRE bacteria have become resistant to most available antibiotics. Infections with these germs are very difficult to treat, and can be deadly. In hospitalized patients with bloodstream infections, CRE mortality has been noted at greater than 40%."

It would be advantageous to have a method for identifying compounds useful for treating bacterial infections including Gram negative (Gm−) bacteria (*Acinetobacter baumannii, E. coli, Klebsiella pneumoniae,* and *Pseudomonas aeruginosa*), as well as a select few Gram positive (Gm+) bacteria, via a new mechanism, particularly one which is unaffected by modes of bacterial resistance, such as those used by carbapenem-resistant Enterobacteriaceae. The present provides such a method, as well as treatment methods using the discovered compounds.

SUMMARY OF THE INVENTION

Methods for identifying specific inhibitors of "selected spectrum bacteria," such as certain Gram negative bacteria and select Gram positive bacteria, isolated tRNA fragments that are useful in these methods, and kits including these fragments, are disclosed. Also disclosed are methods of treating and/or preventing bacterial infections caused by selected spectrum bacteria, using specific inhibitors of the propagation of these bacteria, and pharmaceutical compositions including the inhibitors and a pharmaceutically-acceptable carrier. Combination therapy using one or more of the inhibitors, and a second anti-bacterial compound, are also disclosed.

The inhibition of bacterial propagation results from inhibition of bacterial protein synthesis. In one embodiment, inhibition refers to the selective inhibition of protein synthesis in selected spectrum bacteria in the presence of other bacteria. One advantage of selective inhibition of protein synthesis in selected spectrum bacteria is that, in this manner, the side effects resulting from disturbing beneficial bacteria in the colon, such as *Clostridium difficile* associated diarrhea, CDAD, pseudomembranous colitis, and the like, can be reduced or eliminated. In addition, the selective inhibition by a novel mechanism may reduce the concomitant development of antibacterial resistance in the gastrointestinal tract.

Representative Gram negative bacteria which are "selected spectrum bacteria" include *E. coli*, which causes the majority of urinary tract infections, *Acinetobacter baumanii*, which causes disease mainly in healthcare settings, *Pseudomonas aeruginosa*, which causes bloodstream infections and pneumonia in hospitalized patients, *Klebsiella pneumoniae*, which causes many types of healthcare-associated infections, including pneumonia, urinary tract infections, and bloodstream infections. Representative Gram positive bacteria which are "selected spectrum bacteria" include *Staphylococcus* sp. (incl. *S. aureus* and *S. epidermidis*), *Streptococcus* sp. and *Enterococcus* sp, which use the same Ala ASL as the above-listed Gram negative bacteria.

In one embodiment, the methods for screening inhibitors of propagation of selected spectrum bacteria involve forming a mixture comprising a test compound, a specific sequence of a tRNA anticodon stem loop fragment, and a programmed ribosome capable of binding to the specific tRNA anticodon stem loop fragment. The programmed ribosome includes an mRNA oligomer, tRNA$^{fMet}$, or other appropriate primer, and the ribosome. The mRNA oligomer includes a start codon, and a codon specific for the amino acid of interest (for example, GCA for encoding alanine in those selected spectrum bacteria which use GCA to code for alanine), and may optionally also include one or more of a Shine Delgarno sequence, a box sequence, and codons after the codon for the amino acid of interest.

The mixture is incubated under conditions that allow binding of the tRNA anticodon stem loop fragment and the programmed bacterial ribosome in the absence of the test compound. One can then determine whether or not a test compound inhibits the propagation of selected spectrum bacteria which use a specific ASL, such as ASL$^{Ala}$, which is not used by other bacteria. A compound that interferes with the binding of the tRNA ASL fragment (i.e., inhibits binding, referred to as inhibition, or inhibits release, referred to as agonism) and the ribosome is indicative of the test compound being an inhibitor of the propagation of the selected spectrum bacteria.

In another embodiment, the methods for screening inhibitors of propagation of the selected spectrum bacteria involve forming a mixture comprising a test compound, a specific sequence of a tRNA anticodon stem loop fragment, and a synthetase (in one embodiment, an aminoacyl tRNA synthetase, such as an alanyl tRNA synthetase-AMP) capable of binding to the specific tRNA anticodon stem loop fragment. The synthetase normally forms a complex consisting of the appropriately matched synthetase and amino acid along with AMP. During the second step of this reaction, the appropriately matched tRNA and amino acid are combined with the simultaneous release of AMP and the synthetase.

The mixture is incubated under conditions that allow binding of the appropriately matched tRNA anticodon stem loop fragment and synthetase in the absence of the test compound. One can then determine whether or not a test compound inhibits, or promotes, the binding of the tRNA anticodon stem loop fragment and the synthetase. A compound that interferes with the binding of the tRNA ASL fragment (i.e., inhibits binding, referred to as inhibition, or inhibits release, referred to as agonism) and the synthetase is indicative of the test compound being an inhibitor of bacterial propagation.

The choice of the ASL sequence to use in the screening is made by genomic analysis of tRNA sequences of the bacterial pathogens to be targeted for inhibitor discovery. In one embodiment to screen for Gm-inhibitors the ASL sequence region of four Gram negative (Gm-) bacteria (*A. baumannii*, *E. coli*, *Klebsiella pneumoniae*, and *Pseudomonas aeruginosa*) were compared. It was found at the gene level (DNA) they share four identical ASLs, namely:

| | | |
|---|---|---|
| CCTGCTTTGCACGCAGG Ala | (SEQ ID No. 1) |
| CTACCTTGAGGTGGTAG Leu | (SEQ ID No. 2) |
| CACGCCTGGAAAGTGTG Ser | (SEQ ID No. 3) |
| TCGGGCTCATAACCCGA Met | (SEQ ID No. 4) |

Discovery of an inhibitor that is selective for a common ASL fragment will affect that tRNA for all organisms that contain it. For those bacteria containing that common ASL, they can no longer translate any protein encoded by that tRNA.

The Ala ASL is unique to the codon that it codes for in each of the 4 Gm-organisms listed above (i.e. by knocking out that tRNA, the organisms can no longer translate anything that encodes that codon). It was also confirmed bioinformatically that the post modification pathway is conserved in all 4 pathogens for the Ala tRNA. This is based on finding the AdoMet-MTase superfamily domain conserved across the 4 genomes, as shown below:

>gi1664682453|gb|CP008801.1|:225526-225542
*Escherichia coli* KLY, complete genome: CCTGCTTTGCACGCAGG (SEQ ID No. 1)

>gi1660577155|gb|CP008797.1|:122275-122291 *Klebsiella pneumoniae* subsp. pneumoniae KPNIH24, complete genome CCTGCTTTGCACGCAGG (SEQ ID No. 1)

>gi1648109368|gb|KJ748374.1|:228-244 *Pseudomonas aeruginosa* strain FS-1006 16S ribosomal RNA gene and 16S-23S ribosomal RNA intergenic spacer, partial sequence—CCTGCTTTGCACGCAGG (SEQ ID No. 1)

>gi1640861131|gb|CP007535.1|:343013-343029 *Acinetobacter baumannii* strain AC29, complete genome CCTGCGTGCAAAGCAGG (SEQ ID No. 1)

There are also a few Gram positive bacteria, such as *Staphylococcus* sp. (incl. *S. aureus* and *S. epidermidis*), *Streptococcus* sp. and *Enterococcus* sp, which use the same Ala ASL. Accordingly, the methods described herein can be used to identify compounds which promote binding or inhibit binding of this ASL to the ribosome, or to an aminoacyl synthetase, and will thus act as anti-bacterial agents against these bacteria.

Accordingly, in one embodiment, the methods described herein use the tRNA specific for alanine incorporation in selected spectrum bacteria in a screening method, where the tRNA forms a complex with either a ribosome, or an aminoacyl synthetase. Specific inhibitors of these selected spectrum bacteria, which bacteria use the tRNA specific for alanine incorporation, will interrupt the complex, and therefore prevent alanine incorporation into the growing protein/peptide. This results in bactericidal action.

Once inhibitors and/or agonists are identified, they can be tested in vitro for specific antibacterial activity, for example, by incubating them with other tRNA/ribosome or tRNA/aminoacyl synthetase complexes, to see if they do or do not disrupt these complexes. Alternatively, one can incubate the inhibitors with a variety of bacteria and identify those specific inhibitors of alanine incorporation which are not bactericidal to other bacteria, for example, beneficial bacteria.

In one embodiment, the anti-codon stem loop $ASL^{Ala}$, a tRNA oligomer with the following sequence is synthesized: C C U G C U U cmo5U G C A C G C A G G-Various labels (SEQ ID No. 5) may be attached to either end to facilitate various assay detection technologies. For the assays described in the working examples, FITC was incorporated during synthesis to the 3'-end. An isolated RNA sequence comprising: C C U G C U U cmo5U G C A C G C A G G (SEQ ID No. 5)—either by itself, or with up to 100, up to 50, up to 25, up go 20, or up to 15 base pairs on either or both ends, is intended to be within the scope of the invention.

In another embodiment, the mRNA oligomer for programming the ribosome includes the Shine-Dalgarno (or S-D) sequence, the five to eight nucleotide bases that follow the Shine-Dalgarno sequence, the triplet codon encoding methionine (AUG), which initiates protein translation, and the triplet codon for encoding alanine that is specific for the selected spectrum bacteria, including certain Gram negative and a few Gram positive bacteria.

A representative S-D sequence is AGGAG, and a representative "box" sequence following the S-D sequence is AUAAUAA. A minimal mRNA sequence that includes the S-D sequence, the "box" sequence, the AUG sequence encoding methionine, and the triplet codon encoding alanine (Ala) in certain Gram negative bacteria and a few Gram positive bacteria is provided below:

AGGAGAUAAUAAAUG<u>GCA</u>.(SEQ ID No. 6)

To provide stability, the sequence can include additional bases to the left and right of this sequence. A representative sequence is shown below:

(SEQ ID No. 7)
5'-GGGCGAUAACACUCAGGAGAUAAUAAAUG<u>GCA</u>ACAGCUGAUCAAU

CGUGCAUCC-3'

While other triplet codons can be present before the alanine codon, such would unnecessarily complicate the assay, as one would need to actually translate the intermediate amino acids before arriving at a complex between the ribosome and the $ASL^{Ala}$, which would by necessity include other components in the assay. Additional nucleotides can be present after the $ASL^{Ala}$, and it is actually preferred that such be present, to stabilize the oligonucleotide, even though they will not actually be used to produce a peptide strand, since translation will, ideally, be stopped at the first Ala.

There are four main approaches described herein for inhibiting protein synthesis in selected spectrum bacteria. One is to destabilize the complex formed between the ribosome and the $ASL^{Ala}$, so that the alanine is never added to the protein fragment being transcribed. The other is to overly stabilize the complex, so that translation never proceeds any further. That is, if protein production is inhibited by either blocking the release of the protein fragment from the ribosome, or preventing the addition of alanine to the protein fragment, the bacteria is not viable. If the protein fragment is not released then, further amino acids are not added to the growing peptide chain, and the bacteria is no longer viable. Both types of anti-bacterial agents are intended to be within the scope of the invention described herein.

A third is to destabilize the complex formed between an aminoacyl synthetase and the $ASL^{Ala}$, so that alanine is never added to tRNA required for the protein fragment being transcribed. A fourth is to overly stabilize this complex, so that the $ASL^{Ala}$, is not available for protein synthesis to occur.

While the assay can be used to identify inhibitors of certain Gram negative and a few Gram positive bacteria, all bacteria which can be inhibited using compounds identified using the assays described herein share the same $ASL^{Ala}$. Accordingly, the ribosome can be any ribosome specific for Gram negative bacteria, such as an E. coli ribosome, or any other suitable bacterial ribosome that allows one to form the desired complex, which is then either stabilized or destabilized by the active compounds described herein.

In E. coli, the mRNA consensus sequence 5'AGGAGGU 3' is between 5 and 8 bases upstream from the AUG translation initiation codon (i.e., the codon for methionine). The S-D sequence forms complementary base pairs with a consensus sequence found at the 3' end of the 16S rRNA molecule (q.v.) in the 30S subunit of the ribosome. The S-D sequence thus serves as the binding site for bacterial mRNA molecules on ribosomes.

In one embodiment, the screening assay involves the further step of screening active compounds for their ability to inhibit the propagation of bacteria other than those Gram negative and Gram positive bacteria which use this $ASL^{Ala}$, i.e., which use a different ASL for alanine. In one aspect of this embodiment, this is indicative of compounds that inhibit or stabilize the formation of a complex between the ribosome and the Shine-Delgarno sequence. Where the compounds have broad spectrum antimicrobial activity, and inhibit/promote the formation of a complex between the ribosome and the Shine-Delgarno sequence, the compounds demonstrate a heretofore unknown mechanism of action.

In another embodiment, the screening assay involves the further step of screening active compounds for their ability to inhibit the propagation of bacteria other than those Gram negative and Gram positive bacteria which use this $ASL^{Ala}$, i.e., which use a different ASL for alanine, by screening for the ability of the compounds to inhibit/promote the interaction between other ASLs and an aminoacyl synthetase specific for those ASLs. In one aspect of this embodiment, this is indicative of compounds that inhibit or stabilize the formation of a complex between the aminoacyl synthetase and the $tRNA^{Ala}$. Where the compounds have broad spectrum antimicrobial activity, and inhibit/promote the formation of a complex between the aminoacyl synthetase and the $tRNA^{Ala}$, the compounds demonstrate a heretofore unknown mechanism of action.

Such compounds, and a method of treating bacterial infections using such compounds, are intended to be within the scope of the invention described herein.

Kits for screening inhibitors of the various processes described above are also disclosed. The kits comprise a nucleic acid molecule consisting essentially of a linear sequence of a tRNA anticodon stem loop fragment specific for $ASL^{Ala}$; with or without a detectable label.

In one embodiment, compounds which are inhibitors of the various processes described above can be used in methods of treating and/or preventing infections caused by selected spectrum bacteria, such as those which use the $ASL^{Ala}$. That is, compounds which destabilize or stabilize the complex formed between the mRNA and the ribosome during translation of the codon for alanine that is specific to selected spectrum bacteria, GCA, can inhibit bacterial protein formation. Such methods are also within the scope of the invention.

In other embodiments, the selected spectrum bacteria are those which use the other ASLs described herein (Leu, Met, and Ser), and inhibitory compounds are those which destabilize or stabilize the complex formed between the mRNA and the ribosome during translation of the codon for Leu, Met, or Ser that is specific to the selected spectrum bacteria which use these ASLs.

Rather than destabilizing or stabilizing the complex formed between the mRNA and the ribosome, the inhibitory compounds stabilize or destabilize the complex formed between the tRNA and the appropriate aminoacyl synthetase-AMP. The screening methods used for identifying compounds which inhibit propagation of selected spectrum bacteria which use $ASL^{Ala}$ can be modified, by using a different ASL, to identify compounds which inhibit binding of the programmed ribosome or the appropriate aminoacyl synthetase-AMP to $ASL^{Leu}$, $ASL^{Ser}$, or $ASL^{Met}$. For the programmed ribosome assay, mRNA would include, instead of the specific codon for Ala, the specific codon for Leu, Ser, or Met. For the synthetase assay, the complex would be with the appropriate aminoacyl synthetase and amino acid.

Pharmaceutical compositions useful in these methods are also within the scope of the invention. Such pharmaceutical compositions include one or more inhibitors, as described herein, and a pharmaceutically-acceptable carrier. Combination therapy, using additional antibacterial compounds which function by a different mechanism, is also disclosed.

The foregoing and other objects and aspects of the present invention are explained in detail in the drawings herein and the specification set forth below.

BRIEF DESCRIPTION OF THE DRAWINGS

FIGS. 4A and 4B are illustrations of synthetic oligomers representing the anticodon stem loop useful for the assays described herein. Only when the modifications are present will the ASL bind to programmed ribosomes isolated from Gram negative bacteria, which binding can be detected by monitoring the change in fluorescence.

DETAILED DESCRIPTION

Figure 1:
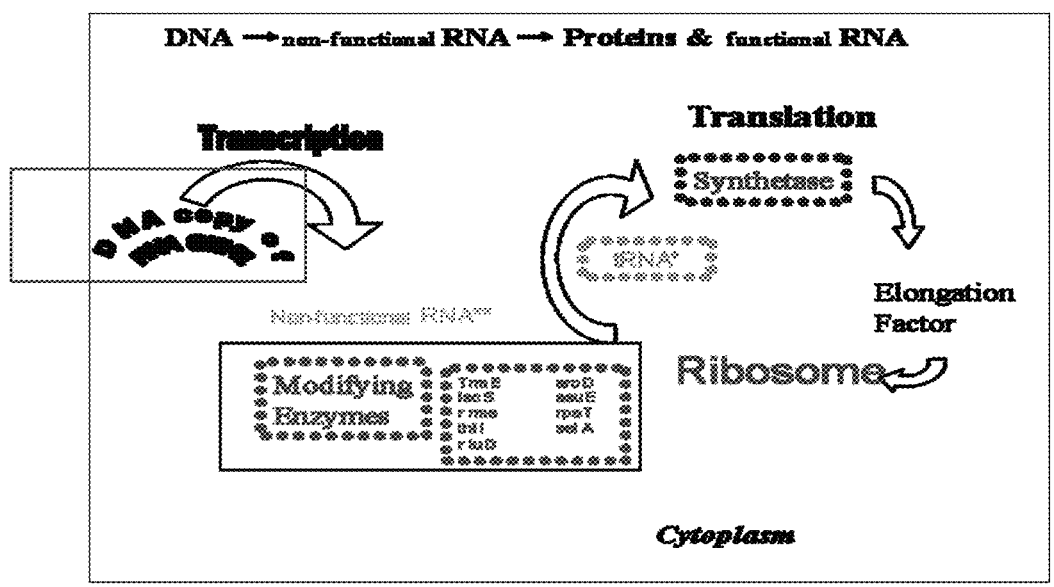
FIG. 1 is a graphic illustration showing the synthesis of proteins via the processes of transcription and translation.

In one embodiment, the present invention relates to compositions and methods for identifying compounds useful for specifically inhibiting the propagation of selected spectrum bacteria, including certain Gram negative bacteria, as well as a few Gram positive bacteria, which use a specific anticodon stem loop, ($ASL^{Ala}$), to produce proteins. Pharmaceutical compositions and methods for treating infections caused by these bacteria are also disclosed. The propagation of these specific bacteria, which use this specific ASL, can be inhibited by inhibiting translation of bacterial RNA into proteins.

The inhibition of translation can occur by promoting or inhibiting the ability of $ASL^{Ala}$ to bind to an aminoacyl synthetase, or promoting or inhibiting the ability of $ASL^{Ala}$ to bind to a ribosome, alone or in the presence of mRNA encoding an alanine. In one aspect, the mRNA is a synthetic sequence that includes a minimal sequence, namely, a Shine-Delgarno sequence, a box sequence, a codon encoding methionine (i.e., a start codon), and the specific codon encoding alanine used by bacteria which use the specific $ASL^{Ala}$ described herein.

In other embodiments, rather than identifying compounds which inhibit propagation of bacteria which use $ASL^{Ala}$, the screening methods identify compounds which inhibit propagation of bacteria which use $ASL^{Leu}$, $ASL^{Met}$, or $ASL^{Ser}$, as described herein. Just as bacteria using $ASL^{Ala}$ were identified using a BLAST search, one of skill in the art can readily identify bacteria using these ASLs by doing a BLAST search, and modify the assays discussed herein which use $ASL^{Ala}$, using the teachings provided herein. The Basic Local Alignment Search Tool (BLAST) is available on-line, and those of skill in the art can readily access this tool on-line. The compounds so identified can be used in methods of treating or preventing infection by these selected spectrum bacteria.

Prior to describing this invention in further detail, however, the following terms will first be defined.

Definitions

As used herein, an "inhibitor" refers to any compound capable of preventing, reducing, or restricting gram negative bacterial propagation. An inhibitor may inhibit the propagation of selected spectrum bacteria, for example, by preventing, reducing or restricting protein formation by selected spectrum bacteria, in one embodiment, specifically by inhibiting alanine incorporation into a growing protein strand. In one aspect, the inhibition of alanine incorporation results from disrupting a complex formed by a tRNA specific for the selected spectrum bacteria's incorporation of alanine into a growing protein strand. In some embodiments, the inhibition is at least 20% (e.g., at least 50%, 70%, 80%, 90%, 95%, 98%, 99%, 99.5%) of the selected spectrum bacterial propagation as compared to the propagation in the absence of the inhibitor. In one aspect, an inhibitor prevents, reduces, or restricts the binding of a tRNA specific to the selected spectrum bacteria, or fragment thereof, to a ribosome, preferably a ribosome associated with protein and peptide synthesis. More particularly, the binding is related to the incorporation or alanine into a growing peptide or protein, and, most particularly, the binding is specific for the incorporation of alanine into a protein or peptide encoded by selected spectrum bacteria, and the tRNA is not useful for the incorporation of alanine into proteins or peptides of other bacteria. In another aspect, an inhibitor prevents, reduces, or restricts the binding of a tRNA specific to the selected spectrum bacteria, or fragment thereof, to an appropriate aminoacyl synthetase.

In one embodiment, as used herein, "selected spectrum bacteria" include Gram negative and Gram positive bacteria that use the $ASL^{Ala}$ described herein. Selected Gram negative bacteria include *Pseudomonas aeruginosa* LESB58, *Klebsiella pneumoniae* 342, *Escherichia coli* O157 H7 EC4115, and *Acinetobacter baumannii* AYE. Selected Gram positive bacteria include *Staphylococcus* sp. (incl. *S. aureus* and *S. epidermidis*), *Streptococcus* sp. and *Enterococcus* sp.

A more complete list of bacteria using this ASL is provided below: *Acinetobacter* sp., erococcus sp., *Aeromonas* sp., noxybacillus sp., Apteryxaustralis antelli, *Bacillus* sp, *Bacteroides* cellulosilyticus, eggiatoa leptomitiformis, Buchnera *aphidicola*, *Campylobacter* sp., Candidatus sp., *Citrobacter* sp., Cronobacter sp., Dickeya *solani*, Edwardsiella sp., *Endozoicomonas montiporae*, *Enterobacter* sp., Enterobacteriaceae bacterium, *Enterococcus* sp., Erysipelotrichaceae bacterium, *Escherichia albertii*, *Escherichia coli*, *Eubacterium* sulci, Faecalibaculum *rodentium*, *Francisella* sp., Gammaproteobacteria bacterium, *Gemella* sp., *Geobacillus* sp., *Halorhodospira halochloris*, *Halotalea alkalilenta*, Halothiobacillus sp., *Helicobacter* sp., Hymenobacter sp., *Klebsiella* sp., *Kluyvera intermedia*, Kosakonia sp., *Lactobacillus* sp., *Lactococcus* sp., *Lentibacillus amyloliquefaciens*, *Leptolyngbya borchgrevinkii*, *Listeria monocytogenes*, *Marinobacterium* sp., *Microbulbifer thermotolerans Oscillatoria* sp., *Ovis canadensis Canadensis Piscirickettsia salmonis*, *Plesiomonas shigelloides*, Pontibacter sp., Pseudanabaena sp., *Pseudomonas* sp., Rufibacter sp., *Salimicrobium jeotgali, Salinicoccus halodurans, Salmonella enterica, Shigella* sp., *Sodalis glossinidius, Staphylococcus* sp. *Streptococcus* sp., *Sulfurovum lithotrophicum*, and *Tetragenococcus halophilus*.

The selection of ASL Ala over ASLs Leu, Ser, or Met reflects additional criteria in target selection. In other embodiments, the selected spectrum bacteria are those which use one or more of ASLs Leu, Ser, or Met.

Figure 3:
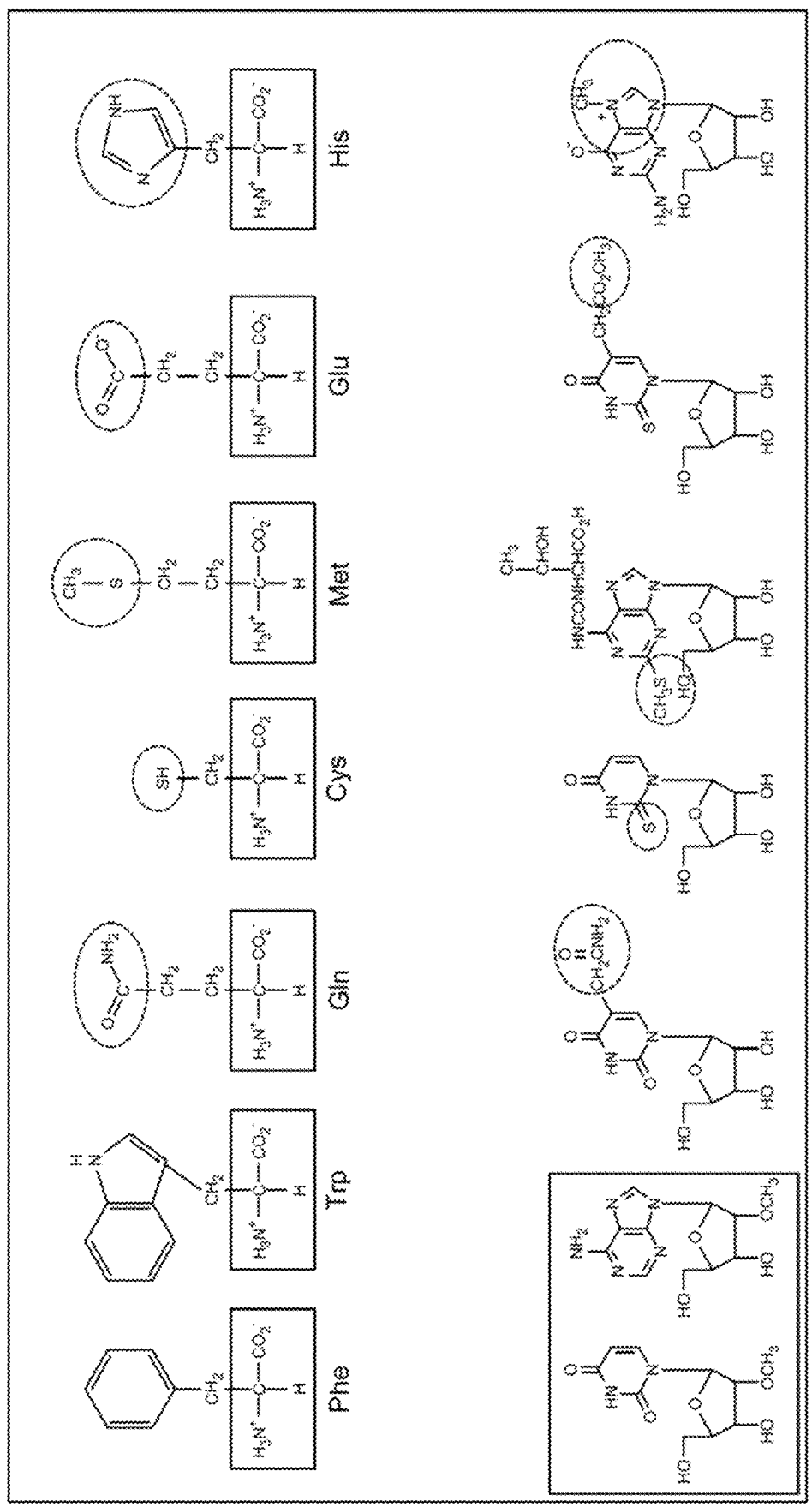
FIG. 3 is a graphic illustration of examples of modified nucleotide bases along bottom row with modifications in circles. Unmodified RNA bases uracil and adenine (in box) are included for comparison. Along the top row are amino acids with functional R-group equivalence to the corresponding nucleotide base in the bottom row.

A feature of all native tRNA is they contain multiple natural enzymatic modifications to the nucleotide bases. (modified nucleotide data base). At least 100 different enzymatic modifications have been identified that result in the addition of R groups to the bases. The chemical R group additions to the nucleotides include, methyl, sulfur, amino acid, and carboxylic acid groups. As shown in FIG. 3, these natural additions to tRNA's have been shown to be essential for normal tRNA function in cellular processes. The tRNA nucleotide base modifications vary between organisms due to genetic differences in the enzyme genes responsible for their additions. The natural modification of the tRNA nucleotides provide additional criteria for the selection of unique targets for therapeutic discovery. The presence of the additional R groups place ligands in the target site that can be exploited in therapeutic selection and provide increased specificity. The genetic difference of the modifying enzymes between organisms provides an additional criteria for selectivity. While some modifying enzymes are common to all organisms, significant cross species and cross kingdom differences exist that provide the opportunity for organism specificity in target selection. The natural modification found in the Ala ASL cmo5U, does provide an additional unique ligand in the target sequence and is only found in a limited number of bacteria and not in eukaryotic cells.

As used herein, a "label" or "detectable label" is any composition that is detectable, either directly or indirectly, for example, by spectroscopic, photochemical, biochemical, immunochemical, or chemical means. Useful labels include, but are not limited to, radioactive isotopes (for example, $^{32}P$, $^{35}S$, and $^3H$), dyes, fluorescent dyes (for example, Cy5 and Cy3), fluorophores (for example, fluorescein), electron-dense reagents, enzymes and their substrates (for example, as commonly used in enzyme-linked immunoassays, such as, alkaline phosphatase and horse radish peroxidase), biotin-streptavidin, digoxigenin, or hapten; and proteins for which antisera or monoclonal antibodies are available. Moreover, a label or detectable moiety can include an "affinity tag" that, when coupled with the target nucleic acid and incubated with a test compound or compound library, allows for the affinity capture of the target nucleic acid along with molecules bound to the target nucleic acid. One skilled in the art will appreciate that an affinity tag bound to the target nucleic acid has, by definition, a complimentary ligand coupled to a solid support that allows for its capture. For example, useful affinity tags and complimentary partners include, but are not limited to, biotin-streptavidin, complimentary nucleic acid fragments (for example, oligo dT-oligo dA, oligo T-oligo A, oligo dG-oligo dC, oligo G-oligo C), aptamers, or haptens and proteins for which antisera or monoclonal antibodies are available. The label or detectable moiety is typically bound, either covalently, through a linker or chemical bound, or through ionic, van der Waals or hydrogen bonds to the molecule to be detected.

The term "host" as used herein refers to human or animal cells or tissues in vitro and human or animal subjects (e.g., avian or mammalian cells, tissues and subjects such as chickens, turkeys, mouse, rat, cats, dogs, cows, pigs, horses, etc.).

The term "ribosome" as used herein refers to both intact active ribosomes and/or ribosome subunits that retain tRNA binding, such as 30S subunits.

As used herein, a programmed ribosome is defined as a ribosome which has come into contact with an mRNA oligo with the specific codon for the amino acid of interest. The mRNA oligo includes at least the start codon for Met, and the codon for the amino acid of interest. It may also include a Shine Delgarno sequence and a box sequence.

As used herein, an aminoacyl synthetase must be specific for the amino acid of interest. For example, where the amino acid is alanine, an alanyl aminoacyl synthetase is used.

The specific tRNA referred to herein with respect to selected spectrum bacteria, including certain Gram negative bacteria and also a few Gram positive bacteria, is preferably a unique or unusual tRNA: that is, one that contains one or more modified bases other than adenine, guanine, cytosine, or uracil in the anticodon binding region (including both the stem and loop thereof), and/or preferably a tRNA that is only found in certain Gram negative bacteria, and a few Gram positive bacteria for binding to a corresponding amino acid (e.g., alanine) during protein translation in these Gram negative and Gram positive bacteria. That is, preferably, the tRNA is specific for alanine, and is only found in these selected spectrum bacteria. A BLAST search of the ALS Ala nucleotide sequence found 169 identical matches, including *A. baumannii, E. coli, Klebsiella pneumoniae,* and *Pseudomonas aeruginosa*. The vast majority were Gm(−) organisms, though a few were Gm(+) organisms. No complete hits were found when this sequence was searched against the *Homo sapiens* database.

Preferably the modified base or bases is/are a nucleotide(s) that is/are at a binding site associated with the ASL region of tRNA as described below (e.g., nucleotides 27-43 using historical tRNA numbering convention) and participates in the binding event. Where carried out in vivo, the tRNA for the corresponding amino acid bound by the selected spectrum bacterial tRNA preferably does not have the same modified base at the binding site or corresponding nucleotide in the host organism (i.e., pathogen specific modification). Many of these exist in the human host and in agronomically important animal hosts as set forth above). Examples of modified bases are set forth below.

Fluorescence Polarization (FP)

Fluorescence polarization (FP) is a homogeneous method that allows rapid and quantitative analysis of diverse molecular interactions and enzyme activities, and has been widely adopted in high-throughput screening (HTS) and small molecule drug discovery.

FP allows one to use fluorescently labeled ligands in binding studies, and differentiate between bound and un-bound ligands. In the instant application, the ASL can be bound to a fluorescent label. When the labeled ASL forms a complex with either a ribosome or an aminoacyl synthetase, the complex formation can be determined using FP.

The principle of FP derives from the fact that the degree of polarization of a fluorophore is inversely related to its molecular rotation, itself being largely driven by Brownian motion. Quantitatively, FP/FA is defined as the difference of the emission light intensity parallel (I∥) and perpendicular (I⊥) to the excitation light plane normalized by the total fluorescence emission intensity.

In use, a fluorophore is excited with light that is linearly polarized by passing through an excitation polarizing filter. The polarized fluorescence is measured through an emission polarizer either parallel or perpendicular, and it can be seen from Equations 1 and 2:

$$FP = I\|-I\bot\|+I\bot \qquad \text{(Equation 1)}$$

and $$FA = I\|-I\bot\|+2I\bot \qquad \text{(Equation 2)}$$

that the FP value is independent of fluorophore concentration as it is not dependent on the absolute intensities of the emission light collected at either orientation. Such an independence of FP on the concentration of the fluorophore reagent (within the limits of instrument linearity and sensitivity) has largely been observed in a very broad spectrum of experimental settings and FP assay formats, and deviation from this relationship can serve as an indicator of fluorescence probe aggregation (anomalous FP increase and premature fluorescence intensity saturation upon increase of fluorophore concentration).

The intrinsic fluorescence intensity (i.e., quantum yield) of a fluorophore may change upon binding to its cognate partner, thus resulting in significantly different contributions of the bound versus free forms of the fluorophore to the total fluorescence intensity of the sample, which in turn can complicate the interpretation of FP measurements.

As instruments may have unequal sensitivity in detecting light in the perpendicular and the parallel orientations, a grating factor (commonly referred to as G factor) has been introduced to correct for that bias in order to calculate absolute polarization values and for cases where data obtained from different instruments are to be compared.

Using these techniques, those of skill in the art can readily determine whether a fluorescently-labeled ASL has bound to a ribosome or to an aminoacylsynthetase-AMP.

I. tRNA Fragments Useful in the Methods Described Herein

The tRNA fragments (or "tool tRNA fragments") for use in the screening methods described herein are tRNA fragments from gram negative bacteria that code for Ala, or, alternatively, Leu, Ser, or Met.

The tRNA fragment ASLs for these amino acids are shown below:

```
CCUGCUUcmo5UGCACGCAGG Ala      (SEQ ID No. 5)

CUACCUUGAGm1G Psi GGUAG Leu    (SEQ ID No. 8)

CACGCCUGGAAAG Psi GUG Ser      (SEQ ID No. 9)

UCGGGCmUCAUAACCCGA Met         (SEQ ID No. 10)
```

Representative tRNA fragments include

```
    CCUGCUUUGCACGCAGG-la-      (SEQ ID No. 11)
    bel Ala

CUACCUUGAGGUGGUAG-la-      (SEQ ID No. 12)
    bel Leu

CACGCCUGGAAAGUGUG-la-      (SEQ ID No. 13)
    bel Ser

UCGGGCUCAUAACCCGA-la-      (SEQ ID No. 14)
    bel Met
```

Each of these fragments, and analogs thereof with one or more modified nucleotides as described herein, represents a separate embodiment of the invention, in that each can be used to identify compounds which inhibit protein synthesis in bacteria which use these specific fragments. While the Ala-associated tRNA fragment is mentioned with more prevalence in the discussion that follows, the Leu, Ser, and Met-associated fragments can also be used to identify inhibitors of protein synthesis in selected spectrum bacteria which use these tRNA to incorporate Leu, Ser, and Met into proteins. Each can be used in assays which involve identifying compounds which promote or inhibit the formation of a tRNA/ribosome complex, or a tRNA/aminoacyl synthetase complex (or, more particularly, a tRNA/aminoacyl synthetase-AMP complex).

In one aspect, the tRNA fragment comprises the nucleic acid sequence CCUGCUUcmo$^5$UGCACGCAGG-Fluorescein (SEQ ID No. 5).

In another aspect, the tRNA fragment is not labeled, but otherwise includes the same sequence, and the promotion or inhibition of binding is determined in a manner which does not involve detection of a label. This is particularly true when the assay involves the promotion or inhibition of the binding of the ASL to an aminoacyl synthetase. In one embodiment, the binding can be determined using an indirect measurement of ATP to AMP using commercially available kits, or, more specifically measuring the disappearance of free ATP or the appearance of free AMP.

In another aspect, the tRNA fragment above can be modified with one or more modified nucleosides, so long as it maintains its selectivity for Ala, or, alternatively, Leu, Ser, or Met and the modified tRNA is still specific for Gram negative bacteria, such as *A. baumannii, E. coli, Klebsiella pneumoniae*, and *Pseudomonas aeruginosa*, as well as those Gram positive bacteria for which the modified tRNA is specific, over other bacteria for which the modified tRNA is not specific.

In one aspect, the tRNA fragment incorporates one, two, three, or more modified nucleosides into the nucleic acid sequence. In another aspect, the tRNA fragments incorporate three modified nucleosides into their nucleic acid sequence. Modified nucleosides that can be incorporated into the tRNA fragments include any modified nucleotide, including, but not limited to unknown modified adenosine (?A), 1-methyladenosine (m1A), 2-methyladenosine (m2A), $N^6$-isopentenyladenosine (i6A), 2-methylthio-$N^6$-isopentenyladenosine (ms2i6A), $N^6$-methyladenosine (m6A), $N^6$-threonylcarbamoyladenosine (t6A), $N^6$-methyl-$N^6$ threonylcarbomoyladenosine (m6t6A), 2-methylthio-$N^6$-threonylcarbamoyladenosine (ms2t6A), 2'-O-methyladenosine I Inosine (Am), 1-methylinosine Ar(p) 2'-O-(5-phospho) ribosyladenosine (m1I), $N^6$-(cis-hydroxyisopentenyl) adenosine (io6A), Unknown modified cytidine (?C), 2-thiocytidine (s2C), 2'-O-methylcytidine (Cm), $N^4$-acetylcytidine (ac4C), 5-methylcytidine (m5C), 3-methylcytidine (m3C), lysidine (k2C), 5-formylcytidin (f5C), 2'-O-methyl-5-formylcytidin (f5Cm), unknown modified guanosine (?G), 2'-O-(5phospho) ribosylguanosine (Gr(p)), 1-methylguanosine (m1G), $N^2$-methylguanosine (m2G), 2'-O-methylguanosine (Gm), $N^2N^2$-dimethylguanosine (m22G), $N^2,N^2$, 2'-O-trimethylguanosine (m22Gm), 7-methylguanosine (m7G), archaeosine (fa7d7G), queuosine (Q), mannosyl-queuosine (manQ), galactosyl-queuosine (galQ), wybutosine (yW), peroxywybutosine (02yW), unknown modified uridine (?U), 5-methylaminomethyluridine (mnm5U), 2-thiouridine (s2U), 2'-O-methyluridine (Um), 4-thiouridine (s4U), 5carbamoylmethyluridine (ncm5U), 5-methoxycarbonylmethyluridine (mcm5U), 5methylaminomethyl-2-thiouridine (mnm5s2U), 5-methoxycarbonylmethyl-2-thiouridine (mcm5s2U), uridine 5-oxyacetic acid (cmo5U), 5-methoxyuridine (mo5U), 5carboxymethylaminomethyluridine (cmnm5U), 5-carboxymethylaminomethyl-2-thiouridine (cmnm5s2U), 3-(3-amino-3-carboxypropyl)uridine (acp3U), 5-(carboxyhydroxymethyl)uridinemethyl ester (mchm5U), 5-carboxymethylaminomethyl-2'-O-methyluridine (cmnm5Um), 5-carbamoylmethyl-2'-O-methyluridine (ncm5Um), Dihydrouridine (D), pseudouridine (ψ), 1-methylpseudouridine (m1ψ), 2'-O-methylpseudouridine (ψm), ribosylthymine (m5U), 5-methyl-2-thiouridine (m5s2U), and 5,2'-O-dimethyluridine (m5Um).

The tRNA fragment may also be any length of a fragment from a tRNA. In one aspect, the tRNA fragment comprises a fragment of between 9 to 15 continuous nucleotides of a tRNA, 10 to 14 continuous nucleotides of a tRNA, or between 11 to 13 continuous nucleotides of a tRNA. In another aspect, the fragment is a fragment of 8, 9, 10, 11, 12, 13, 14, 15, or 16 continuous nucleotides of a tRNA. In a further aspect, the fragment is a fragment of 12 continuous nucleotides of a tRNA.

The tRNA fragment may or may not be capable of forming a secondary structure. In a one aspect, the tRNA fragment is not capable of forming a stem loop structure with itself. In another aspect, the fragment is a linear fragment of a tRNA that is not capable of forming a stem loop structure with itself.

The tRNA fragment may also be linked to additional nucleic acids. For example, the tRNA fragment may be linked to one or more additional nucleic acids depending on the assay method. In one aspect, the tRNA fragment may be linked to nucleotides used to attach the fragment to a solid support surface. In another aspect, the fragment tRNA is linked to additional nucleic acid molecules at one or both terminal end of the tRNA fragment. In another aspect, the fragment tRNA is linked to additional nucleic acid molecules at both terminal ends. The additional nucleic acid sequences can be any length, preferably between 8 and 16 nucleotides, between 10 and 14 nucleotides, more preferably 12 nucleotides in length. In one aspect, the terminal sequences do not allow the tRNA fragment to form a secondary structure, such as a hairpin loop structure.

The specific tRNA referred to herein with respect to host tRNA is also preferably a unique or unusual tRNA: that is, one that contains one or more modified bases other than adenine, guanine, cytosine, or uracil in the anticodon binding region (including both the stem and loop thereof), as set forth above, and/or preferably one that is the only tRNA available in that host for binding to RNA for priming of translation of selected spectrum bacterial proteins.

The region of the tRNA to which binding occurs as described herein is, in general, the tRNA anticodon stem-loop structure, and most preferably the loop structure itself. Following conventional tRNA nucleotide numbering (see, e.g., M. Sprinzl et al., Compilation of tRNA sequences and sequences of tRNA genes, Nucleic Acids Res. 26, 148-153 (1998)), the site to which binding occurs is from nucleotides 27-43 of said tRNA. Binding may be to a single site or combination of sites comprising nucleotides within this range.

As noted above, methods of screening for compounds useful for inhibiting the propagation of those selected spectrum bacteria are disclosed herein. In one embodiment, the method involves contacting a specific bacterial tRNA, such as a specific tRNA$^{ala}$, which is specific for the selected spectrum bacteria, but not to many other Gram positive or Gram negative bacteria, to a ribosome that binds that tRNA in the presence of the test compound. The contacting step is typically carried out in vitro in an aqueous solution, with the tRNA, the ribosome, an appropriate messenger RNA, and the test compound in the aqueous solution. The contacting step may be carried out with a single test compound or with a library of probes or test compounds in any of a variety of combinatorial chemistry systems, as discussed in greater detail below. If the compound inhibits or promotes the complex formed between the tRNA and the ribosome, the compound is an inhibitor of bacterial propagation, for those bacteria which use the specific tRNA in bacterial propagation.

After the contacting step, the next step involves determining whether the compound inhibits the binding of the specific tRNA to the ribosome (in one embodiment, the binding of tRNA$^{ala}$ at the appropriate position(s) on the ribosome for incorporation of an alanine into a growing peptide or protein).

In another embodiment, rather than evaluating the ability of the test compounds to inhibit/promote the tRNA/ribosome complex formation, the ability of the test compounds to inhibit/promote the tRNA/aminoacyl synthetase complex formation is evaluated. If the compound inhibits or promotes the complex formed between the tRNA and the aminoacyl synthetase, the compound is an inhibitor of bacterial propagation, for those bacteria which use the specific tRNA in bacterial propagation.

The general equations for the biology that occurs during protein translation are shown below:

$$\text{amino acid} + \text{ATP} \rightarrow \text{aminoacyl-AMP} + \text{PPi} \qquad 1$$

$$\text{aminoacyl-AMP} + \text{tRNA} \rightarrow \text{aminoacyl-tRNA} + \text{AMP} \qquad 2$$

So, one can begin the reaction by combining the appropriately matched aminoacyl synthetase enzyme, amino acid, and ATP, and hold this complex basically at the end of reaction 1.

Test compounds and the tRNA oligo (ASL) can then be added. If the reaction goes to completion, forming the aminoacyl-tRNA complex, one can then measure the appearance of AMP (the appearance of which indicates that the reaction is not inhibited) or the lack of appearance of AMP (which indicates that the compound promoted or inhibited the complex formation, which also indicates that the compound is active at inhibiting bacterial propagation). Because the appearance of AMP can be measured, the ASL need not include a label. If using a labeled tRNA oligomer, one can measure the formation or lack of formation of the tRNA/synthetase complex using methods such as fluorescence polarization.

In either embodiment, the determining step can be carried out by any suitable means, such as the filter binding assays disclosed below, or in any of the binding detection mechanisms commonly employed with combinatorial libraries of probes or test compounds as discussed below. Inhibition of ribosomal binding by the test compound indicates that the test compound is useful for inhibiting bacterial propagation, with respect to those bacteria which use the specific tRNA used in the assay. Compounds identified by this technique are sometimes referred to as "active compounds" herein. The method is particularly useful for identifying compounds that inhibit bacterial growth, preferably bacteria that contain a single tRNA for a particular amino acid, such as a single alanine tRNA that is specific for certain specific bacteria, including the Gram negative and Gram positive bacteria described elsewhere herein, over other Gram negative and Gram positive bacteria.

A method of screening for compounds useful for preferentially inhibiting bacterial propagation in a host is also disclosed herein. The method comprises contacting the specific host tRNA to the bacterial RNA (i.e., tRNA from the selected spectrum bacteria which use an RNA sequence unique to these bacteria, and not used by many other bacteria) in the presence of the test compound. The contacting step is typically carried out in vitro in an aqueous solution, with the tRNA, the bacterial RNA, and the test compound in the aqueous solution. The term "bacterial RNA" is intended to encompass both a complete bacterial genome and fragments thereof that contain the tRNA binding portions (such fragments will typically be at least 10 or 12 to 50 or more nucleotides in length) of those Gram negative and Gram positive bacteria which use one or more of the unique RNA sequences described herein, such as the unique ASL$^{Ala}$, or in other embodiments, the unique ASL$^{Leu}$, ASL$^{Ser}$, or ASL$^{Met}$ described herein.

The contacting step may again be carried out with a single test compound or with a library of probes or test compounds in any of a variety of combinatorial chemistry systems, as discussed in greater detail below.

After the contacting step, the next step involves determining whether the compound inhibits the binding of the specific host tRNA to the bacterial RNA in the presence of the test compound. The determining step can be carried out by any suitable means, such as gel shift assays, chemical and enzymatic footprinting, circular dichroism and NMR spectroscopy, equilibrium dialysis, enzymatic crystallography, or in any of the binding detection mechanisms commonly employed with combinatorial libraries of probes or test compounds as discussed below.

The inhibition of binding indicates that the test compound is useful for inhibiting propagation of the bacteria in a host, such as a human, animal, or plant. Such compounds are also sometimes referred to as "active compounds" herein. The method may be carried out, for example, with the selected spectrum bacteria described herein. In one embodiment the specific host tRNA is mammalian, preferably primate or specifically human, such as tRNA$^{ala}$, and the determining step comprises determining whether the compound inhibits the binding of tRNA$^{ala}$ to the bacterial RNA.

As noted above, the present invention can be used with test compounds (or "probe molecules"), or libraries (where groups of different probe molecules are employed), of any type. In general, such probe molecules (including those that are active compounds herein) are organic compounds, including oligomers such as antisense oligonuleotides, non-oligomers, organo-metallic compounds, and combinations thereof, as well as bio-inorganic compounds. Non-oligomers include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, benzodiazepenes, terpenes, prophyrins, toxins, and combinations thereof. Oligomers include peptides (that is, oligopeptides) and proteins, oligonucleotides such as DNA, RNA and their derivatives such as peptide nucleic acid (PNA), oligosaccharides, polylipids, polyester, polyamides, polyurethans, polyureas, polyethers, poly(phosphorus derivatives) such ass phosphates, phosphonates, phosphoramides, phosphonamides, phosphites, phosphinamides, etc., poly(sulfur derivatives) such as sulfones, sulfonates, sulfites, sulfonamides, sulfenamides, etc., where for the phosphorous and sulfur derivatives the indicated heteroatom for the most part will be bonded to C, H, N, O or S, and combinations thereof. Numerous methods of synthesizing or applying such probe molecules on solid supports (where the probe molecules may be either covalently or non-covalently bound to the solid support) are known, and such probe molecules can be made in accordance with procedures known to those skilled in the art. See, e.g., U.S. Pat. No. 5,565,324 to Still et al., U.S. Pat. No. 5,284,514 to Ellman et al., U.S. Pat. No. 5,445,934 to Fodor et al. (the disclosures of all United States patents cited herein are to be incorporated herein by reference in their entirety); J. Baldwin and I. Henderson, Recent Advances in the Generation of Small-Molecule Combinatorial Libraries: Encoded Split Synthesis and Solid-Phase Synthetic Methodology, Med. Res. Reviews 16, 391-405 (1996).

Such probe molecules or active compounds could be used as inhibitors by contacting the tRNA, the RNA to which the tRNA binds (mRNA, ribosomal RNA) or the modification enzyme responsible for the unique or unusual chemistry or structure of the tRNA (i.e., the modified base).

II. Synthetases in Protein Synthesis

The specific nucleotide sequence of an mRNA specifies which amino acids are incorporated into the protein product of the gene from which the mRNA is transcribed, and the role of tRNA is to recognize the sequence from the genetic code and transfer the correct amino acid.

One section of the anticodon stem loop of the tRNA matches the genetic code in a three-nucleotide sequence called the anticodon. The anticodon forms three base pairs with a codon in mRNA during protein biosynthesis. The mRNA encodes a protein as a series of contiguous codons, each of which is recognized by a particular tRNA. On the other end of the tRNA is a covalent attachment to the amino acid that corresponds to the anticodon sequence. Each type of tRNA molecule can be attached to only one type of amino acid, so each organism has many types of tRNA (in fact, because the genetic code contains multiple codons that specify the same amino acid, there are several tRNA molecules bearing different anticodons which also carry the same amino acid).

The covalent attachment to the tRNA 3' end is catalyzed by enzymes called aminoacyl tRNA synthetases or synthestase(s) that are specific for each amino acid i.e. alanyl tRNA synthetase is specific for alanine). During protein synthesis, tRNAs with attached amino acids are delivered to the ribosome by proteins called elongation factors (EF-Tu in bacteria, eEF-1 in eukaryotes), which aid in decoding the mRNA codon sequence. If the tRNA's anticodon matches the mRNA, another tRNA already bound to the ribosome transfers the growing polypeptide chain from its 3' end to the amino acid attached to the 3' end of the newly delivered tRNA, a reaction catalyzed by the ribosome.

III. Methods for Identifying an Inhibitor of Selected Spectrum Bacterial Propagation Inhibitors of bacterial propagation, where the bacteria are certain Gram negative or Gram positive bacteria which use a unique ASL not used by the vast majority of other bacteria to code for a specific amino acid, can be identified using the methods described herein. The bacterial propagation can be inhibited, for example, by inhibiting bacterial translation of RNA to proteins.

The scientific rationale behind the methods for identifying inhibitors of bacterial propagation, and a way to carry out the method, are discussed below.

Identifying Inhibitors of Bacterial Protein Translation

In one aspect, the method can be used to identify inhibitors of bacterial translation/protein expression, for those selected spectrum bacteria described herein. In another aspect, the methods can be used to identify inhibitors of tRNA binding to a target nucleic acid molecule. In another aspect, the methods can be readily adapted for use in high through-put assays. Transfer RNA (tRNA) is involved in translation through the recognition of a corresponding site on the mRNA priming translation. Identifying inhibitors of translation/protein expression can lead to the identification of therapeutic compounds for use in treating or preventing infections by one or more of the selected spectrum bacteria in a host cell and organism.

In one embodiment, the method comprises forming a mixture having a tRNA anticodon stem-loop (ASL) fragment, a target nucleic acid molecule that is capable of binding to the tRNA fragment, and a test compound. In one aspect, the target nucleic acid molecule corresponds to a fragment of the bacterial genome involved in translation (for those selected spectrum bacteria described herein), specifically, involved in incorporation of alanine residues, and, more specifically, incorporation of alanine residues using a tRNA specific for these bacteria, as described elsewhere herein, into a protein or peptide necessary for the bacteria to survive.

The resulting mixture is incubated under conditions that allow binding of the tRNA fragment and the target nucleic acid in the absence of the test compound. The method further involves detecting whether the test compound inhibits the binding of the tRNA fragment to the target nucleic acid, where the absence of binding of the tRNA ASL fragment and the target nucleic acid molecule is indicative of the test compound being an inhibitor of the specific type of bacterial propagation being screened for. In one aspect, the detection involves the use of labels to detect the inhibition of binding of the tRNA fragment to the target nucleic acid molecule.

Protein Synthesis

One pathway ideally suited for novel antibiotic discovery is protein synthesis, which involves the ribosome and several types of enzymes. Both the ribosome and the enzymes bind to specific RNA sequences (FIG. 1). What is lacking for the discovery of new classes of antibiotic compounds that target protein synthesis at the ribosome is a method by which to screen large numbers of compounds that may interfere with these RNA interactions. Ashraf (1999), Phelps (2004) and others have discovered that the ribosome:RNA interactions occur at a much higher frequency and with greater affinity in regions of the RNA that contain modified nucleotide bases.

As shown in FIG. 1, protein synthesis requires the involvement of nonfunctional RNA. The nonfunctional RNA(**) which is a substrate of the modifying enzyme is converted to functional RNA either by modifying one or more nucleotide bases. The anticodon stem loop (ASL) of tRNA(*) that contains modified nucleotide bases interacts with the ribosome to transfer specific amino acids to the on-going protein synthesis process.

Figure 2:
FIG. 2 is a graphic illustration showing tRNA binding to the P, A and E sites on the ribosome.

Recent crystallographic investigations illustrate that the post-transcriptional modifications of some tRNAs play an essential role in tRNA recognition by the ribosome translocation site (Phelps et. al. 2004, FIG. 2). These crystallographic studies of the ribosome with ASLs have revealed that the basis for tRNA recognition is a specific group of modified ribosomal residues (FIG. 2).

In addition, binding studies utilizing synthetic RNA oligomers representing the ASL that contains various modified nucleotide bases have also demonstrated an increased affinity of the ribosome with the oligomer containing the modified nucleotide base(s) over the RNA oligomers with unmodified nucleotide bases.

The Role of Modified Nucleotides in Translation

The academic research in the labs of Dr. Paul Agris, NC State University, and Dr. Andrzej Malkiewicz, of the Technical University of Lodz, Poland has focused on understanding a narrow area of RNA biology (See, for example, U.S. Pat. No. 6,461,815). Their research has focused on understanding the role of the natural post-transcriptional modifications in RNA structure and function (Agris et. al. 2004). These modifications are enzyme catalyzed and can be as simple as the addition of a methyl group or they can be quite complex, involving a multi-enzyme process.

The details of tRNA$^{ala}$ binding and the critical role of tRNA modifications have been determined at the ribosomal translocation site. FIG. 2 is a recently resolved structure of a tRNA$^{ala}$ ASL bound to the ribosome at the translocation site of *Thermus thermophilus* (Schuette et. al., 2009). The atomic resolution structure provides evidence that the basis for increased binding of the native modified tRNA$^{Lys}$ ASL compared to an unmodified ASL is specific atomic interactions with the modified base. While the structural details are less understood, modifications to the nucleotide bases in the anticodon stem loop of tRNA significantly increase the affinity of tRNA to the ribosome at both A and P binding sites (Ashraf et. al. 1999).

Over 100 different naturally occurring modified nucleotides are found in all classes of RNA and all kingdoms of organisms (Limbach et. al. 1994). One to two percent of all RNA nucleotides are modified. These nucleotide base modifications are frequently found near catalytic sites of RNAs and many of the proteins that are responsible for the modification are encoded by essential genes (Zhang 2004). In FIG. 3, the modified portions of some example nucleotide bases are circled along with the corresponding site on different amino acids to highlight the area of interaction and increased chemical affinity between the nucleotide base and the amino acid. The researchers in Agris and Malkiewicz labs have taken an approach to study model systems produced by chemical synthesis methods rather than using modified nucleotide bases obtained from biochemical methods (Agris et. al. 1995). This synthetic approach provides far more control to investigate, in detail, the significant contributions made by modified nucleotides. Studies using synthetic nucleotide bases have demonstrated the essential role that RNA modifications have in binding at the ribosome as well as in protein synthesis (Hermann, 2005; Francois, et. al. 2005). This approach has also been used in biophysical studies to determine the thermodynamic contribution of modifications (Agris et. al. 1999). In structural studies, this synthetic approach has been able to demonstrate the role of the modified nucleotide basis in producing new structures which are critical in functional capacities (Agris, et. al. 1997).

Similarly, tRNA containing modified nucleotides plays a key role in matching the correct amino acid with the correct tRNA in reactions catalyzed by some synthetases.

The aminoacyl synthetases have been investigated as targets for antibiotic therapy for many years (Kim et. al. 2003). Synthetases are essential and clinically validated as target for antibiotics, with natural products, including mupirocin found to be effective (Ward et. al. 1986). Further screening by HTS have discovered bioactive compounds; however, most lacked the selectivity or bioavailability to be effective therapeutics (Vondenhoff, et. al., 2011). One way to overcome this limitation is to utilize identity elements within synthetase(s) that are very selective to a single organism or group of organisms (Xu, et. al. 2014). It has been recently reported that for the Gram negative *E. coli* the modified nucleotide threonylcarbamoyladenosine (t6A) located in the anticodon stem loop of tRNA acts as an identity element for some synthetases (Thiaville et. al. 2015). This study found the synthetase was 25 time more active on a modified substrate than an unmodified transcript. The tRNA modification identity elements are not universal in all organisms and they have the potential to be exploited as therapeutic targets (Aldinger, et. al. 2012). The presence of modified nucleotides in the anticodon is not limited to just *E. coli* with numerous examples found and characterized (Juhling, et. al. 2009).

Synthesis of Modified Nucleotides and Oligomers

As noted above, a key advancement in elucidating the role and importance of post-transcriptional modification in tRNA binding to the ribosome is the development of synthetic approaches to produce tRNA mimics (Agris, et. al. 1995). The first step in producing the synthetic tRNA mimics is the synthesis of the modified nucleotide bases, also known as phosphoramidites (Agris et al 1995). The modified bases are then used during the synthesis of the RNA oligomers (Ogilvie et. al. 1988). Synthetic approaches overcome the substantial barrier of obtaining sufficient amounts of natural products for the functional characterization studies. In addition to providing the fully modified ASL for characterization of the tRNA:ribosome binding, the synthetic approach allows for the preparation of intermediate forms of the modified material that can further elucidate the individual contribution of each modification step in enhanced tRNA binding. These mimics have been used to demonstrate that the nucleotide modifications to the anticodon increase the affinity of the tRNA for the ribosome by three orders of magnitude (Ashraf, et. al. 1999; Preliminary Data Section 4).

An additional constraint in exploiting these post translational nucleotide base modifications as potential targets is the lack of methods to efficiently synthesize the modified RNA oligomers which incorporate the modified nucleotide bases. This research group has discovered and/or licensed the necessary technology to allow for the synthetic preparation of significant quantities of these natural products (Agris et. al. 1995). In combination with commercially available standard bases, protocols have been developed to allow for the incorporation of hyper-modified nucleotides (phosphoramidites) into oligomers in quantities sufficient to use in RNA based screening assays.

With the oligomers containing modified nucleotide bases, the present inventors have conducted preliminary experiments related to some of the key components required for the development of these assays. These preliminary experiments validate this concept for the discovery of inhibitors with pharmaceutical potential. The HTS screening assay described herein identifies small molecule inhibitors for development of antibiotics. Specifically, these inhibitors interfere the binding of the tRNA with the ribosome during translation, or interfere with the binding of the tRNA to an aminoacyl synthetase.

Characterization of tRNA Binding to the Ribosome In Vitro.

Several laboratories have demonstrated that the binding of tRNA to programmed ribosomes can be replicated in vitro (von Ahsen 1997 Ashraf 1999). Schilling-Bartetzko et. al. (1992) discovered that ribosomes could be purified and programmed with a message and that tRNA would bind to various sites on the ribosome based on the solution conditions. These binding reactions are currently performed as individual reactions with the ASL:ribosome complex being bound to filter papers. In addition to these reactions being conducted in a large volume, they use radioactive materials for detection and quantitation. While these methods do provide an approach to characterize tRNA:ribosome binding they are not compatible with HTS assays due to the size of the reaction vessel, the radioactive detection methodology, and the subsequent radioactive waste disposal. A fluorescent method of detection to monitor tRNA binding to the ribosome has been developed (Wells et. al. 1980) that can be adapted to an HTS format.

Figure 5:
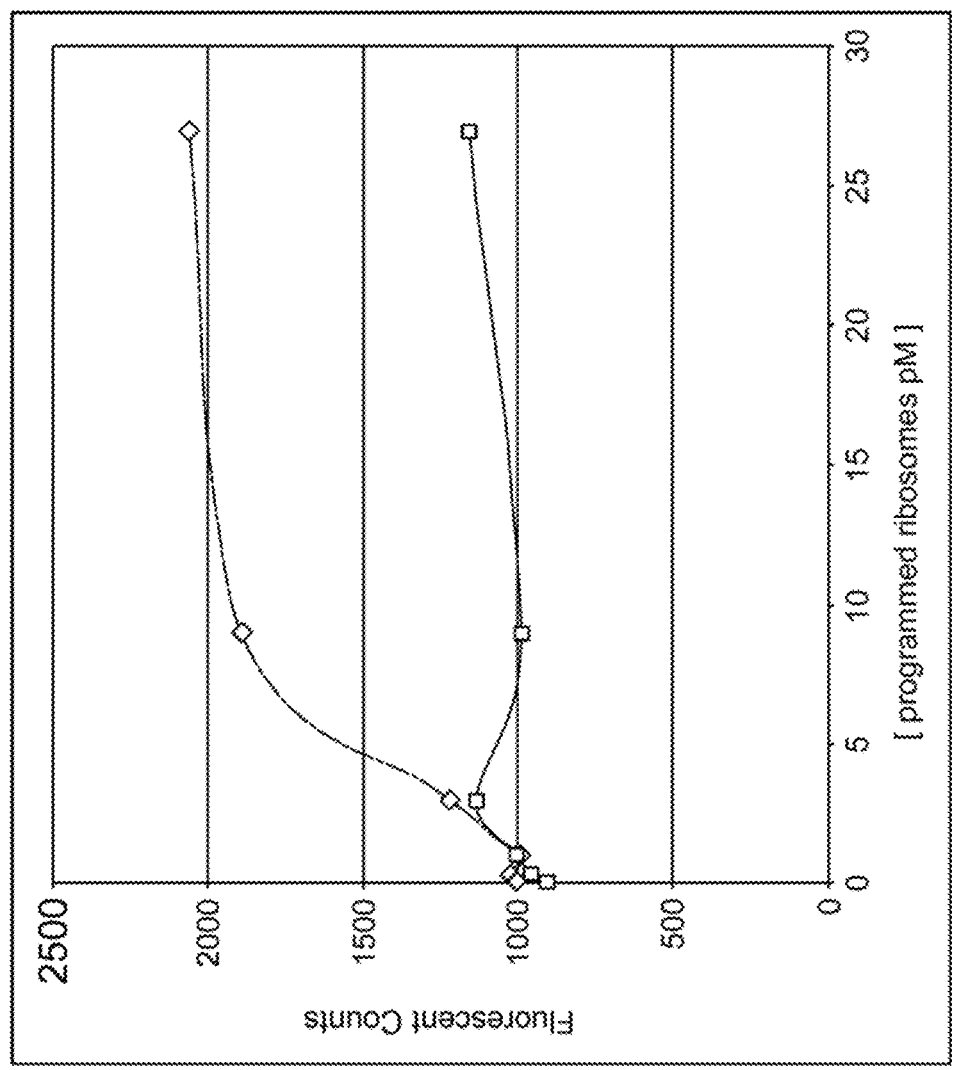
FIG. 5 is a chart showing the titration of fluorescently labeled ASL with programmed ribosomes (dashed line) and unprogrammed ribosomes (solid line). Compounds that alter the complex (destabilize or stabilize) will result in changes to the fluorescent signal.

Preliminary Data:

Combining all of the facts from above (translation as a biochemical target; ASL of tRNA containing modified nucleotides are essential to translation; that one can synthesize the modified bases and RNA oligomers containing these modified bases; and, that these oligomers bind to programmed ribosomes), the present inventors have conducted a series of experiments to demonstrate that a fluorescently labeled synthetic oligomer containing 17 nucleotide bases, 2 of which are modified, (FIG. 4A) will bind to programmed ribosomes isolated from Gram positive bacteria, and that this binding can be detected by monitoring the change in fluorescence (FIG. 5). An additional oligomer is shown in FIG. 4B.

In moving from a manual radioactive filter based assay to a format suitable for adaptation to a HTS format, efforts were focused in two objectives. Concurrent efforts were made on the preparation of the phosphoramidite components for the synthesis of a modified oligonucleotide while experiments were performed to adapt the assay format.

Developing high throughput assays to identify compounds that inhibit RNA:ribosome interactions is the basis of this application. The development of this HTS assay requires several components including: selection and synthesis of the substrates (oligomers which contain modified nucleotides); detection methodologies; conversion of standard methods to high throughput methods; and, proof that these RNA oligomers will serve as ribosome substrate in an HTS assay.

Preliminary data to support the selection of the RNA oligomer to use as a substrate for this assay, the assay format (filter paper vs. in solution), and for the assay conditions were generated by Trana scientists. As described in the following paragraphs Trana scientists have obtained preliminary data to support: (1) the selection of the RNA oligomer to use as a substrate for this assay; (2) the assay format (filter paper vs. in solution), and (3) the assay conditions.

Selection of test sequence.

The initial survey of the modification requirement for an ASL to bind to the ribosome (Yarian 2002) identified several different ASL where the unmodified oligomer poorly bound to programmed ribosomes. These ASLs become good candidates for tools to be used to screen for compounds that can block selected tRNA from binding to the ribosome and selectively inhibit bacterial protein synthesis. Based on the phosphoramidites available for oligonucleotide synthesis, tRNA$^{Ala}$ was selected. Using the complete genome for four Gm-bacteria (*A. baumannii* AYE, *E. coli* 0157, *Klebsiella pneumoniae*, and *Pseudomonas aeruginosa* LESB58), FIG. 4 is an illustration of a synthetic oligomer representing the anticodon stem loop from tRNA$^{Ala}$ in these specific Gram negative bacteria.

Synthesis of Modified Nucleotide Base(s) and RNA Oligomers

Using a combination of methods from the literature and proprietary information, the present inventors have developed protocols for the synthesis, incorporation and purification of all the modified nucleotides found in the tRNA$^{Ala}$ ASL from Gram negative bacteria (Vendeix 2008).

In general, functional groups on the modified nucleotide bases are protected using phosphoramidite chemistry (Ogilvie et. al. 1988). Using this chemistry, the founders have incorporated over 20 different modified nucleotides into a range of oligonucleotides ranging in length from 3 to 36 nucleotides (Nobles et. al. 2002). The protecting groups were subsequently removed after synthesis of the RNA oligomer. The addition of a protecting group to each modified base and ribose is described below. Because the 2 position thio-groups in the modified RNA nucleotides can be oxidized in standard RNA synthesis an alternative oxidizing agent, tert-butyl hydroperoxide (10% solution in acetonitrile) (Kumar and Davis, 1997), was used during synthesis of the oligomer along with other proprietary techniques. The founders have used these synthetic RNA oligomers in both functional (Yarian 2000, 2002 and Phelps 2004) and structural studies (Stuart 2000 and Murphy 2004).

Synthesis of RNA Oligomers Containing Modified Nucleotide Bases

The RNA oligomer was synthesized and purified following protocols developed specifically for these modified reagents (Agris et. al. 1995, Murphy et. al. 2004). Purification of the oligomers was by HPLC as previously described (Agris et. al., 1999). Purity of the oligomer was confirmed by gel electrophoresis and proper incorporation of the modified nucleotide bases was confirmed by mass spectrometry. In general the synthesis of an RNA oligomer requires that all of the major functional groups on each nucleotide base be protected during the formation of the oligomer and then deprotected after synthesis.

Deprotection of Synthetic Oligoribonucleotides (RNA Oligos)

Several protecting groups are available and are selected based upon the specific chemistry of each nucleotide base; thus, the protection group on the RNA phosphoramidite monomers to a large extent will dictate the strategy for deprotection. It is routine in the art to remove silyl protecting groups with tetrabutylammonium fluoride solution and triethyamine trihydrifluoride.

For regular deprotection of the phosphoramidite protecting groups, ethanolic ammonium hydroxide is added to the vial containing the beads from the synthesis process and incubated—time specific to the types of protecting groups. For removal of the Silyl protecting groups on the sugars, tetrabutylammonium fluoride solution is added to the residue from deprotection step. The 4 steps described in the following paragraphs are required to add each nucleotide to the oligomer.

Step A: De-Blocking

The first base, which is attached to the solid support, is at first inactive because all the active sites have been blocked or protected. To add the next base, the DMT group protecting the 5'-hydroxyl group must be removed. This is done by adding a base, either dichloroacetic acid (DCA) or trichloroacetic acid in dichloromethane (DCM), to the reaction column. The 5'-hydroxyl group is now the only reactive group on the base monomer. This ensures that the addition of the next base will only bind to that site. The reaction column is then washed to remove any extra acid and by-products.

Step B: Base Condensation

The next base monomer cannot be added until it has been activated. This is achieved by adding tetrazole to the base. Tetrazole cleaves off one of the groups protecting the phosphorus linkage. This base is then added to the reaction column. The active 5'-hydroxyl group of the preceding base and the newly activated phosphorus bind to loosely join the two bases together. This forms an unstable phosphite linkage. The reaction column is then washed to remove any extra tetrazole, unbound base and by-products.

Step C: Capping

When the activated base is added to the reaction column some does not bind to the active 5'-hydroxyl site of the previous base. If this group is left unreacted in a step it is possible for it to react in later additions of different bases. This would result in an oligonucleotide with a deletion—and an incorrect sequence manufactured. To prevent this from occurring, the unbound, active 5'-hydroxyl group is capped with a protective group which subsequently prohibits that strand from growing again. This is done by adding acetic anhydride and N-methylimidazole to the reaction column. These compounds only react with the 5'-hydroxyl group. The base is capped by undergoing acetylation. The reaction column is then washed to remove any extra acetic anhydride or N-methylimidazole.

Step D: Oxidation

In step 2 the next desired base was added to the previous base, which resulted in an unstable phosphite linkage. To stabilize this linkage a solution of dilute iodine in water, pyridine, and tetrahydrofuran (when synthesizing DNA) is added to the reaction column. For RNA syntheses, see previous paragraphs describing our techniques for consideration made at this step. The unstable phosphite linkage is oxidized to form a much more stable phosphate linkage.

Repeat above steps for entire sequence being synthesized.

Steps one through four are repeated until all desired bases have been added to the oligonucleotide. Each cycle is approximately 94/95% efficient in unmodified RNA and approximately 91/92% efficient in highly modified units of RNA phosphoramidites incorporated into oligonucleotides.

Post Synthesis Treatment to Remove Protecting Groups

After all bases have been added, the oligonucleotide must be cleaved from the solid support and deprotected before it can be effectively used. This is done by incubating the chain in appropriate solutions previously described. Once all the protecting groups are cleaved, including the cyanoethyl group, the heterocyclic protection groups, and the DMT group, the oligonucleotide will be functional and ready to use.

Use of Combinatorial Chemistry Screening to Identify and Optimize Leads

Mechanistically and biologically active hits can be identified using compound libraries, such as lead generation libraries, i.e., libraries including between around 10 and around 500,000 compounds. This risk can be minimized by selecting a diverse library; however, subsequent screening of another library is also a possibility. The assay can be used to identify active compounds that are specific to selected pathogens.

As presented in the preliminary data, for those embodiments where the assay involves detecting compounds which inhibit the complex formed between the tRNA (ASL) and the ribosome, the substrates (an RNA oligomer containing modified nucleotide bases and the bacterial ribosomes, which in some embodiments are Gram negative bacterial ribosomes) to be used in this assay have been synthesized. The RNA oligomer can include a Shine Delgarno sequence, a box sequence, the codon for Met, and the codon for Ala (or, in other embodiments, Ser, Leu, or Met).

Once leads are identified, mammalian cell toxicity testing can be conducted, and computational modeling can also be conducted.

The assay can be automated, or can be run manually. The manual assay can be conducted, for example, in 96-well plate format. The conversion of this assay to HTS format typically involves reducing the volumes of the kit components for use in a 384 or possibly 1,536 plate format, and optimizing the conditions for the capabilities available with a given robotic system. For example, during the early phase of development of the manual assay, the assay mixture was incubated at 37° C. following previous protocols; however, incubating at this temperature is difficult to accomplish in some facilities. To compensate for this, preliminary experiments were conducted to determine that incubation at 25° C., but for a longer period of time, can be used.

When the volume of all substrates is reduced, the amount of the fluorescent label is also reduced; thus, reducing the amplitude of the signal to be detected. This is generally overcome by using detectors specifically developed for HTS assays or using other means to increase the signal differential between bound vs. unbound substrate. To ascertain the effect of the assay reagents and/or assay conditions on assay performance, each condition can be varied within predetermined ranges and the assay results will be analyzed as described below. Assay conditions can be modified, for example, until a Z-factor between 0.4 and 1 is obtained (see next paragraph). Z-factors are an industry standard method for determining when an assay has been optimized.

To calculate the Z-factor, data from the optimization experiments will be recorded electronically, stored to disk, and directly imported into an electronic spreadsheet for analysis. Data will be analyzed to determine the assay value ratio (AVR) defined as 3(Sp+Sb)/(Xt-Xb), where: Sp and Sb are standard deviation of positive control signal and background signal; and, Xp and Xb are the averages of the positive control totals and backgrounds (Zhang, et. al. 1999). A value of less than 0.6 indicates suboptimal assay performance. The Z factor is determined as (1-AVR); therefore, the target value is between 0.4 and 1.0.

The HTS assay can be validated, for example, by analyzing a suitable library (for example, including approximately 6,000 compounds including positive and negative controls) in duplicate using the HTS robotic systems.

An industry standard diverse chemical library (eg., Preswick library) supplemented in random order with positive and negative controls along with other selected chemicals can be used in this validation experiment. During the first run, this validation will demonstrate that the positive and negative controls can be determined in a consistent manner and that a range of activity is detected in the remaining compounds. This will demonstrate that the assay is robust and functioning properly on the complete robotic system.

Typically, if the assay is determined not to be robust, then some mechanical aspect of the robotic system needs to be evaluated. For example, the stability of reagents and substrates in the tubing and mechanical portions of the robotic systems may be the cause of the inconsistent results. These challenges are generally not insurmountable, just time consuming and causing delays in the project. In some cases if the results are totally unacceptable, then the first day results are discarded and this experiment is rerun after identifying and fixing the item(s) that caused the inconsistent results. After the first day experiment is completed with acceptable results, the experiment is repeated on a second day simply to confirm the results from the first experiment.

In addition to the positive and negative controls, the validation library contains compounds that are generally known to be general toxins that will inhibit most assays. Another criterion for assay validation is the ability of the assay to identify these general toxins while not being inhibited by all compounds in the library.

Figure 6:
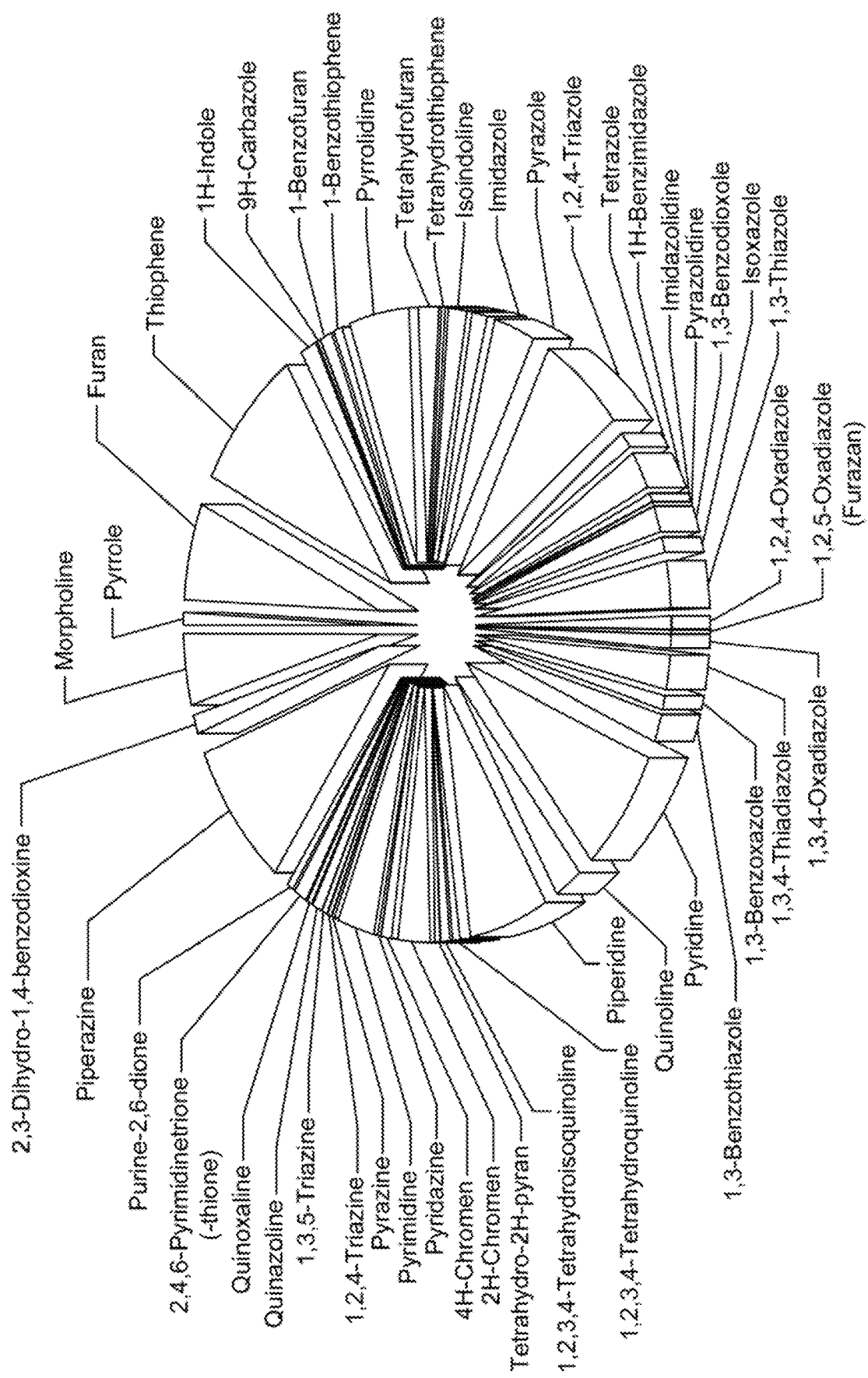
FIG. 6 is a chart showing the chemical diversity of a representative 100 k compound library.

A diverse chemical library can be screened using the validated assay. As used herein, the term library refers to 100 or more compounds, ideally, 10,000 or more compounds, and preferably, includes a minimum of 100,000 compounds or more. A subset of a diverse chemical library will be screened with the validated assay at a single concentration. Ideally, diverse and targeted libraries will total approximately 500,000 compounds, consisting of a mix of structurally diverse singletons and compound clusters. The clusters are ideally built around a variety of scaffolds, each class containing enough members to provide a preliminary SAR analysis if the entire cluster is screened. The libraries ideally include a modest selection of natural products and known drugs, though natural products were not emphasized during compound acquisition because of their frequent synthetic intractability. The collection has been characterized for diversity (for example, by Tanimoto coefficients, as implemented in the Selector software module of the SYBYL modeling package), and individual members have been characterized for biological relevance by, for example, their Lipinski parameters and molecular fingerprints known to favor small molecule-protein interactions. The anticipated distribution of one 100 k subset, which is a representative compound library, is depicted in FIG. 6. Portions of this library have been screened in over 80 assays with over 16,000 hits confirmed in dose response studies.

Depending upon the throughput of the validated assay (384 vs. 1,536 plate format), this typically takes one or two days on a robotic system, and approximately one week for data analysis. In a typical screening campaign, 3 to 5% of the compounds are expected to demonstrate some level of activity. Those compounds that demonstrate sufficient inhibitory activity in the assay can be re-screened in a dilution series (5 to 10 concentrations) to confirm that the compounds are inhibitory and to establish $IC_{50}$ and $IC_{90}$ concentrations. A range of inhibitory activity is typically observed in these experiments. Generally, those compounds referred to as 'hits' that demonstrate the strongest inhibitory effects (lower inhibitory concentrations) are selected for advancement to the next step, for example, subsequent screening in biological assays as described herein.

In some cases, a manual review of the chemical structures of the compounds demonstrating inhibitory activity will be conducted by an expert in structure-activity-relationships, and compounds that are less inhibitory will also be selected for further screening based on favorable chemical structure characteristics.

Confirming the Biological Activity of Hits from the HTS

The biological activity of the identified 'hits' from the screening assays described above can be determined by analyzing these hits in a minimum inhibitory compound bacterial screen.

Screening of the 'hits' for antimicrobial activity to determine 1) a single breakpoint concentration of activity against a common Gram-positive bacteria, and a Gram-negative or Gram positive human pathogen which uses one of the specific ASLs described herein; and 2) whether a "clinically significant" potency can be detected using a threshold concentration of 32 µg/ml. For determining the single breakpoint of activity against a panel of pathogens including *Pseudomonas aeruginosa*, *Staphylococcus aureus*, *Streptococcus agalactiae* (Strep. Group B), *Streptococcus pneumoniae*, *Streptococcus pyogenes* (Strep. Group A), *Klebsiella pneumoniae*, *Escherichia coli*, *Enterococcus faecalis* and *Acinetobacter baumannii*. As a minimum inhibitory concentration (MIC), an achievable potency of less than or equal to 32 µg/ml would be considered an active sample worthy of extended study.

The process can use the reference broth microdilution methods recommended by the Clinical and Laboratory Standards Institute (CLSI; formerly the National Committee for Clinical Laboratory Standards [NCCLS]) M7-A7 document. A 96 well microtiter tray assay will be used to test a single concentration of 32 µg/ml against each pathogen species. A working concentration of 64 µg/ml can be made using appropriate solvents and diluents. A calibrated pipette can be used to transfer 50 µL of each sample into one well of each of three 96-well microtiter plates. A standard inoculum (equivalent to a 0.5 MacFarland standard) of each microorganism can be made in Mueller-Hinton broth and 50 µL of a diluted sample to achieve $3-5 \times 10^5$ CFU/ml can be added to each sample diluting the sample 1:1 to a final test concentration of 32 µg/ml. Each batch of samples can include two internal quality controls using antimicrobial agents with a known potency range and targeting protein syntheses. A positive growth control with only growth support media and an ethanol control at concentrations equivalent to that in the samples can also be tested for each pathogen. After the broth microdilution plates are inoculated, they are incubated in an ambient air environment at 35° C. for 20-24 hours. The plates are removed from incubation and each well is inspected for growth. If a well is clear of growth (non-turbid), an MIC of <32 µg/ml is achieved and the sample is defined as an active sample and subject to further investigation.

Those compounds that are determined to be active at a single concentration can then be tested in a dilution series against the same organisms. Those compounds that are the most active can be advanced to the secondary screen described in the next paragraph. The conduct of these first two screens on a limited number of species can allow for a greater number of compounds active at the molecular level to be tested at the whole organism level increasing the opportunity to identify biologically active compounds in a very cost effective manner.

A secondary screen of "active" samples can include an extended dilution screen (eight to 12 $\log_2$ dilution steps) to determine "on-scale" value for a potential antimicrobial agent including evaluation of breadth of spectrum to such organisms including staphylococci, streptococci, Enterobacteriaceae, non-fermentative Gram-negative bacilli, Gram-positive bacteria, single cell eukaryotes, anaerobes and yeast species. These isolates are, in one embodiment, recent clinical strains representing wild-type and strains with resistance phenotypes. Methods utilized include those described above, and can also involve the addition of NCCLS M11-A6 (anaerobes) and M7-A2 (yeast). Testing against this broader spectrum of organisms can better characterize the spectrum of antimicrobial activity. In one embodiment, the compounds are effective against selected spectrum bacteria, but not against other bacterial species.

The conduct of the initial MIC and the secondary antimicrobial screening can follow industry accepted methodologies and carry no risk in regards to the ability to conduct this testing.

Estimating the Mammalian Toxicity of Biologically Active Compounds

The potential mammalian toxicity of biologically active compounds identified in the assays described herein can be estimated using mammalian cell lines. Compounds that are highly toxic in these assays can be considered to be general toxins with a high probability of interacting with multiple molecular targets. Cytotoxicity assays can be conducted, for example, with rat hepatoma H4IIE cell line, rat kidney NRK cell line, and/or primary human hepatocytes. Each cell line can be exposed to 5 concentrations of each test article or with appropriate positive and negative control substances. Where all three cell lines are used, these three biochemical endpoints can be monitored to determine viability, mitochondrial function, and membrane integrity.

The assay described herein can be used to better understand the tRNA ribosome interactions that occur during translation, and used to screen large compound libraries to discover novel antibiotics. The lead compounds identified during the automated HTS can be further developed for the treatment of bacterial infections caused by one or more of the selected spectrum bacteria. The new antibiotics can reduce the potential for the development of drug resistance and for the treatment of currently-existing multi-drug resistant organisms.

IV. Pharmaceutical Compositions

The selective bacterial inhibitors described herein can be incorporated into pharmaceutical compositions and used to treat or prevent a condition or disorder in a subject susceptible to such a condition or disorder, and/or to treat a subject suffering from the condition or disorder. The pharmaceutical compositions comprise an active compound or a pharmaceutically acceptable salt thereof, in any pharmaceutically acceptable carrier.

Optically active compounds can be employed as racemic mixtures, as pure enantiomers, or as compounds of varying enantiomeric purity. The pharmaceutical compositions described herein include the inhibitors and a pharmaceutically acceptable carrier and/or excipient.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form. Compositions including a liquid pharmaceutically inert carrier such as water or other pharmaceutically compatible liquids or semisolids may be used. The use of such liquids and semisolids is well known to those of skill in the art.

The compositions can also be administered via injection, i.e., intravenously, intramuscularly, subcutaneously, intraperitoneally, intraarterially, intrathecally; and intracerebroventricularly. Intravenous administration is a preferred method of injection. Suitable carriers for injection are well known to those of skill in the art, and include 5% dextrose solutions, saline, and phosphate buffered saline. The compounds can also be administered as an infusion or injection (e.g., as a suspension or as an emulsion in a pharmaceutically acceptable liquid or mixture of liquids).

If a solution is desired, water is the carrier of choice with respect to water-soluble compounds or salts. With respect to the water-insoluble compounds or salts, an organic vehicle, such as glycerol, propylene glycol, polyethylene glycol, or mixtures thereof, may be suitable. In the latter instance, the organic vehicle may contain a substantial amount of water. The solution in either instance may then be sterilized in any suitable manner, preferably by filtration through a 0.22 micron filter. Subsequent to sterilization, the solution may be filled into appropriate receptacles, such as depyrogenated glass vials. Of course, the filling should be done by an aseptic method. Sterilized closures may then be placed on the vials and, if desired, the vial contents may be lyophilized.

In addition to active compounds or their salts, the pharmaceutical compositions may contain other additives, such as pH adjusting additives. In particular, useful pH adjusting agents include acids, such as hydrochloric acid, bases or buffers, such as sodium lactate, sodium acetate, sodium phosphate, sodium citrate, sodium borate, or sodium gluconate. Further, the compositions may contain anti-microbial agents. Useful antimicrobial agents include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In yet another aspect of the present invention, there is provided an injectable, stable, sterile composition comprising an active compound or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into man. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

The formulations may also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

Other pharmaceutical compositions may be prepared from the active compounds, such as aqueous base emulsions. In such an instance, the composition can contain a sufficient amount of pharmaceutically acceptable emulsifying agent to emulsify the desired amount of the active compound or salt thereof. Particularly useful emulsifying agents include phosphatidyl cholines, and lecithin.

Further, the present invention provides liposomal formulations of the active compounds or salts thereof. The technology for forming liposomal suspensions is well known in the art. When the active compound or salt thereof is an aqueous-soluble salt, using conventional liposome technology, the same may be incorporated into lipid vesicles. In such an instance, due to the water solubility of the compound or salt, the compound or salt can be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Another type of delivery is by implantable drug delivery depots, which typically include a hydrophilic biocompatible, and optionally biodegradable polymer with the active agent physically contained within the structure. The active agent is released by its permeation of and diffusion through the polymer or copolymer structure. The depot may be designed to release the substance or substances at predetermined rates and in predetermined sequence. One type of depot system is of the kind disclosed in U.S. Pat. No. 4,450,150, in which the co-polymer is a poly(glutamic acid-co-ethyl glutamate) co-polymer, which ultimately biodegrades to glutamic acid. Other suitable depot based drug delivery vehicles include polyethylene glycol, and copolymers thereof. Among the preferred configurations for the depots are rods and closed-end capsules.

Pharmaceutical formulations are also provided which are suitable for administration as an aerosol, by inhalation. These formulations comprise a solution or suspension of the desired active compound or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the compound, or a salt thereof, in any appropriate manner known in the art, such as by micronization. Most preferably, the size of the solid particles or droplets can be from about 1 to about 2 microns. In this respect, commercial nebulizers are available to achieve this purpose.

Preferably, when the pharmaceutical formulation suitable for administration as an aerosol is in the form of a liquid, the formulation can comprise a water-soluble active compound or a salt thereof, in a carrier which comprises water. A surfactant may be present which lowers the surface tension of the formulation sufficiently to result in the formation of droplets within the desired size range when subjected to nebulization.

Exemplary methods for administering such compounds will be apparent to the skilled artisan. The usefulness of these formulations may depend on the particular composition used and the particular subject receiving the treatment. These formulations may contain a liquid carrier that may be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, the compositions are administered such that active ingredients interact with regions where microbial infections are located. The compounds described herein are very potent at treating these microbial infections.

In certain circumstances, the compounds described herein can be employed as part of a pharmaceutical composition with other compounds intended to prevent or treat a particular microbial infection, i.e., combination therapy. In addition to effective amounts of the compounds described herein, the pharmaceutical compositions can also include various other components as additives or adjuncts.

Combination Therapy

The combination therapy may be administered as (a) a single pharmaceutical composition which comprises an inhibitor as described herein, at least one additional pharmaceutical agent described herein, and a pharmaceutically acceptable excipient, diluent, depot, such as a polyethylene glycol depot, or carrier; or (b) two separate pharmaceutical compositions comprising (i) a first composition comprising an inhibitor as described herein and a pharmaceutically acceptable excipient, diluent, depot, or carrier, and (ii) a second composition comprising at least one additional pharmaceutical agent described herein and a pharmaceutically acceptable excipient, diluent, depot, or carrier. The pharmaceutical compositions can be administered simultaneously or sequentially and in any order.

In use in treating or preventing microbial disease, the inhibitors can be administered together with at least one other antimicrobial agent as part of a unitary pharmaceutical composition. Alternatively, it can be administered apart from the other antimicrobial agents. In this embodiment, the inhibitors and the at least one other antimicrobial agent are administered substantially simultaneously, i.e. the compounds are administered at the same time or one after the other, so long as the compounds reach therapeutic levels for a period of time in the blood.

Combination therapy involves administering the inhibitors, as described herein, in combination with at least one anti-microbial agent, ideally one which functions by a different mechanism (i.e., by penetrating the bacterial cell wall, or interfering with one or more receptors and/or enzymes in the bacteria).

Representative Antibacterial Compounds

Examples of antibacterial compounds include, but are not limited to, aminoglycosides, ansamycins, carbacephems, carbapenems, cephalosporins (First, Second, Third, Fourth and Fifth Generation), glycopeptides, macrolides, monobactams, penicillins and beta-lactam antibiotics, quinolones, sulfonamides, and tetracyclines.

Representative aminoglycosides include Amikacin, Gentamicin, Kanamycin, Neomycin, Netilmicin, Streptomycin, Tobramycin, and Paromomycin. Representative ansamycins include Geldanamycin and Herbimycin. These agents function by binding to the bacterial 30S or 50S ribosomal subunit, inhibiting the translocation of the peptidyl-tRNA from the A-site to the P-site and also causing misreading of mRNA, leaving the bacterium unable to synthesize proteins vital to its growth.

Loracarbef is a representative carbacephem. Representative carbapenems include Ertapenem, Doripenem, Biapenem, Imipenem/Cilastatin, and Meropenem.

Representative first generation cephalosporins include Cefadroxil, Cefazolin, Cephalothin, and Cephalexin. Representative second generation cephalosporins include Cefaclor, Cefamandole, Cefoxitin, Cefprozil, and Cefuroxime. Representative third generation cephalosporins include Cefixime, Cefdinir, Cefditoren, Cefoperazone, Cefotaxime, Cefpodoxime, Ceftazidime, Ceftibuten, Ceftizoxime, and Ceftriaxone. Cefepime is a representative fourth generation cephalosporin, and Ceftobiprole is a representative fifth generation cephalosporin.

Representative glycopeptides include Teicoplanin and Vancomycin, which function by inhibiting peptidoglycan synthesis.

Representative macrolides include Azithromycin, Clarithromycin, Dirithromycin, Erythromycin, Roxithromycin, Troleandomycin, Telithromycin, and Spectinomycin, which function by inhibiting bacterial protein biosynthesis by binding irreversibly to the subunit 50S of the bacterial ribosome, thereby inhibiting translocation of peptidyl tRNA.

Aztreonam is a representative monobactam.

Representative penicillins include Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, and Ticarcillin. These can be administered with an agent which inhibits beta-lactamase enzymatic activity, such as potassium clavanulate or clavulanic acid.

Representative quinolones include Ciprofloxacin, Enoxacin, Gatifloxacin, Levofloxacin, Lomefloxacin, Moxifloxacin, Norfloxacin, Ofloxacin, and Trovafloxacin.

Representative sulfonamides include Mafenide, Prontosil, Sulfacetamide, Sulfamethizole, Sulfanilimide, Sulfasalazine, Sulfisoxazole, Trimethoprim, and Trimethoprim-Sulfamethoxazole (Co-trimoxazole) (TMP-SMX).

Representative tetracyclines and tetracycline-like compounds include Glycylcycline class antibiotics such as Tigecycline; Demeclocycline, Doxycycline, Minocycline, Oxytetracycline, and Tetracycline.

Other antibacterial agents include, for example, Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampin or Rifampicin, and Tinidazole.

V. Methods of Using the Compounds and/or Pharmaceutical Compositions

The compounds can be used to treat or prevent specific microbial infections caused by those Gram negative and Gram positive bacteria which use one or more of the unique ASLs described herein for protein translation. The compounds can also be used as adjunct therapy in combination with existing therapies in the management of the aforementioned types of infections. In such situations, it is preferably to administer the active ingredients to a patient in a manner that optimizes effects upon the selected spectrum bacteria, including drug resistant versions, while minimizing effects upon normal cell types. While this is primarily accomplished by virtue of the behavior of the compounds themselves, this can also be accomplished by targeted drug delivery and/or by adjusting the dosage such that a desired effect is obtained without meeting the threshold dosage required to achieve significant side effects.

Bacterial propagation can be selectively inhibited by inhibiting ribosomal binding of a specific tRNA useful for incorporation of alanine into a growing peptide or protein in the specific Gram negative or Gram positive bacteria which use this specific tRNA, by an amount sufficient to inhibit bacterial propagation, while not inhibiting protein synthesis in other bacteria. Inhibition of ribosomal binding may be carried out by contacting an active compound to the ribosome in an amount effective to inhibit binding sufficiently to inhibit selected spectrum bacterial propagation. The selected spectrum bacteria may be in vitro, in a culture media, or on a surface to be disinfected, or may be in vivo in a host (e.g., a human or animal host in need of an antimicrobial treatment). Formulations of active compounds can be prepared and administered in accordance with known techniques, as discussed below.

One embodiment of a method of specifically inhibiting bacteria propagation in a host, for selected spectrum bacteria which use a specific host tRNA, comprises inhibiting or promoting the binding of the specific host tRNA to the bacteria RNA at one of the binding sites by an amount sufficient to inhibit propagation of the bacteria in the host.

Another embodiment of a method of specifically inhibiting bacteria propagation in a host, for bacteria which use a specific host tRNA, comprises inhibiting or promoting the binding of the specific host tRNA to an aminoacyl synthetase, or, more specifically, to an aminoacyl-AMP, by an amount sufficient to inhibit propagation of the selected spectrum bacteria in the host.

Formulations of active compounds can be prepared and administered in accordance with known techniques, as discussed below. In a preferred embodiment, the specific host tRNA is tRNA$^{Ala}$. Preferably the selected spectrum bacteria primes translation specifically with the specific host tRNA, such as tRNA$^{Ala}$. The host may be a cell in vitro, or a human or animal subject in need of such treatment.

Subjects to be treated by the methods of the present invention are typically human subjects although the methods may be carried out with animal subjects (dogs, cats, horses, cattle, etc.) for veterinary purposes. The present invention provides pharmaceutical formulations comprising the active compounds, including pharmaceutically acceptable salts thereof, in pharmaceutically acceptable carriers for aerosol, oral, and parenteral administration as discussed in greater detail below. The therapeutically effective dosage of any specific compound, the use of which is in the scope of present invention, will vary somewhat from compound to compound, patient to patient, and will depend upon the condition of the patient and the route of delivery.

In accordance with the present method, an active compound or a pharmaceutically acceptable salt thereof, may be administered orally or through inhalation as a solid, or may be administered intramuscularly or intravenously as a solution, suspension, or emulsion. Alternatively, the compound or salt may also be administered by inhalation, intravenously or intramuscularly as a liposomal suspension. When administered through inhalation the active compound or salt should be in the form of a plurality of solid particles or droplets having a particle size from about 0.5 to about 5 microns, preferably from about 1 to about 2 microns.

The present invention will be better understood with reference to the following non-limiting examples.

Example 1: Working Assay Protocol for a HTS Assay to Identify Inhibitors of Selected Spectrum Bacterial Propagation The following is a general example of the screening assay described herein. The exact quantities of reagents are representative only, and are not intended to be limiting.

In this assay, the programmed ribosome is prepared such that it is ready to complex with the tRNA oligomer. Test compounds are added and if the test compound interferes (inhibits or stabilizes) with the subsequent binding of the tRNA to the ribosome complex, the detected signal will be altered. For this assay, measurements are taken at two time points. The first time point will measure inhibition of binding. The second time point, when compared to untreated controls, will measure the stabilization of the complex as the ribosome—tRNA complex will normally dissociate over time.

Assay Target: Ribosome of Gram negative bacteria programmed with Ala message (for example AGGAGAUAAUAAAUGGCA) (SEQ ID No. 6)
Assay tool: ASL of Gram Negative Bacterial tRNA Ala with FL label (for example CCUGCUUUGCACGCAGG-label) (SEQ ID No. 11)
Sample detection method: —Currently fluorescence quenching but can convert to time resolved fluorescence polarization.
Sample format 96 and 384 well plates (other plate formats can be used if desired)
   Sample volume: 100 µl and 5 µl
   Target concentration: 5 pM
   Tool concentration: 10 pM
   DMSO concentration 10%
Materials
   Isolated Ribosome (2 pM/µl)
   Message 2 ug/µl (mRNA oligomer)
   ASL 3-6 ug/µl
   CMN buffer—80 mM potassium cacodylate, pH 7.2, 20 mM $MgCl_2$, 100 mM $NH_4Cl$, and 3 mM β-mercaptoethanol
Method—96 well format
1. Prepare programmed ribosome as follows:
   a. Mix 5 pM per well,
   b. Add 2 µg message
   c. Add 0.3-10 pM ASL
   d. Add 10p test compound
   e. Adjust to 100 µl volume
2. Incubate the mixture for a sufficient time and at a sufficient temperature to allow formation of a complex. Representative conditions include a 20 minute incubation period, at a temperature of around 37C, to allow for complex formation.
3. Read the fluorescence on plate reader. Results similar to those shown in FIG. 5 will be obtained when formation of the complex is altered over time.

Example 2: Prophetic Screening Assay Using an Aminoacyl-Synthetase

The following is a general example of the screening assay described herein using an appropriate aminoacyl-synthetase.

The addition of an amino acid to its appropriate tRNA is a two-step reaction (see below) catalyzed by the appropriate synthetase. During this reaction, the synthetase will form a complex in step 1 and be released upon the completion of the reaction in step 2. This assay is designed to measure either the release of AMP in step 2 (using unlabed tRNA oliogomer) or the formation of the complex between the synthease and the tRNA oliogomer (using labeled tRNA oligomer).

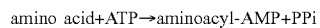

amino acid+ATP→aminoacyl-AMP+PPi     1

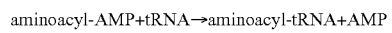

aminoacyl-AMP+tRNA→aminoacyl-tRNA+AMP     2

This example assay is to measure the release of AMP at the completion of reaction 2.
Assay Target: appropriate amino acyl synthetases for example alanyl tRNA synthetase
Assay tool: ASL of tRNA Ala containing modified nucleotide bases
Sample detection method: —In this example, the assay uses an indirect measure of the conversion of the energy source, ATP and AMP. Other detection such as fluorescence quenching time resolved fluorescence polarization, fluorescence, etc. could also or alternatively be used.
Sample format 96, 384, or 1,536 well plates
   Sample volume (adjusted for the appropriate plate): 100p and 5µl
   Target concentration: 5 pM
   Tool concentration: 10 pM
   DMSO concentration 10% or less
Materials
   Synthetase isolated from a gram neg bacteria that is a selected spectrum bacteria, or produced using a microbial clone
   ATP
   ASL 3-6 ug/µl
   buffer
   may or may not use secondary detection of AMP
Method—
4. Prepare enzyme mixture with ATP either with (control samples), or without, putative inhibitor compounds (test samples), and detect components for producing or consuming AMP:
   a. Mix in each well,
   b. Add Tool (tRNA$^{Ala}$ oligomer)
5. Incubate according to instructions on commercial kit used for measuring AMP. Representative incubation times/temperatures are usually in the range of around 20 min at a temperature of around 37° C., although longer times can be used, and temperatures can be above or below this value, and 6. Read fluorescence, luminescence, or other appropriate signal on the plate reader. The amount of AMP produced is directly proportional to the activity of the synthetase. If synthetase activity is inhibited, then no AMP is produced. If no AMP is produced, then the compound is considered active. If AMP is produced, then the compound is considered inactive.

LITERATURE CITED

The following references were cited herein, and the contents of these references, and all other references cited herein, are hereby incorporated by reference in their entirety.

Aldinger C A, Leisinger A K, Igloi G L, *FEBS Journal* 2012 279 3622-3638 The influence of identity elements on the aminoacylation of tRNA$^{Arg}$ by plant and *Escherichia coli* arginyl-tRNA synthetases.

Agris P F. Decoding the genome: a modified view. Nucleic Acids Res. 2004 Jan. 9; 32(1):223-38. Print 2004. Review.

Agris P F, Malkiewicz A, Kraszewski A, Everett K, Nawrot B, Sochacka E, Jankowska J, Guenther R. *Biochimie*. (1995) Site-selected introduction of modified purine and pyrimidine ribonucleotides into RNA by automated phosphoramidite chemistry. 77(1-2):125-34.

Agris P F, Guenther R, Ingram P C, Basti M M, Stuart J W, Sochacka E, Malkiewicz A. (1997) Unconventional structure of tRNA(Lys)SUU anticodon explains tRNA's role in bacterial and mammalian ribosomal frameshifting and primer selection by HIV-1. RNA. 1997 April; 3(4):420-8.

Agris P F, Guenther R, Sochacka E, Newman W, Czerwinska G, Liu G, Ye W, Malkiewicz A. (1999) Thermodynamic contribution of nucleotide modifications to yeast tRNA(Phe) anticodon stem loop analogs. *Acta Biochim Pol*. 1999; 46(1):163-72.

Ashraf S S, Sochacka E, Cain R, Guenther R, Malkiewicz A, Agris P F. RNA (1999) Single atom modification (O→S) of tRNA confers ribosome binding. (2):188-94.

Ashraf S S, Ansari G, Guenther R, Sochacka E, Malkiewicz A, Agris P F. (1999) The uridine in "U-turn": contributions to tRNA-ribosomal binding. RNA. 1999 April; 5(4): 503-11.

CDC 2000-2001. "Drug Resistance/Antimicrobial Resistance", Centers for Disease Control and Prevention, CDC Fact Book 2000/2001, p. 75.

CDC 2013 Morbidity and Mortality Report 62(09) p 165-170.

DRAGON. http://www.disat.unimib.it/chm/Dragon.htm. 2005. Ref Type: Electronic Citation Francois B, Russell R J, Murray J B, Aboul-ela F, Masquida B, Vicens Q, Westhof E. *Nucleic Acids Res*. (2005) Crystal structures of complexes between aminoglycosides and decoding A site oligonucleotides: role of the number of rings and positive charges in the specific binding leading to miscoding. 33 (17):5677-90.

Grosjean, H. and Benne, R. Modification and editing of RNA. Washington, D C ASM Press, c1998.

Hermann T. *Curr Opin Struct Biol*. (2005) Drugs targeting the ribosome. 15(3):355-66.

Jühling F, Marl M, Hartmann R K, Sprinzl M, Stadler P F, and Putz *J. Nucleic Acids Res.,* 2009 37, tRNAdb 2009: compilation of tRNA sequences and tRNA genes.

Kim S, Lee S W, Choi E C, Choi S Y. *Appl Microbiol Biotechnol*. 2003 61(4):278-88. Aminoacyl-tRNA synthetases and their inhibitors as a novel family of antibiotics.

Kumar R K, Davis D R. Synthesis and studies on the effect of 2-thiouridine and 4-thiouridine on sugar conformation and RNA duplex stability. *Nucleic Acids Res.* 1997 Mar. 15; 25(6):1272-80.

Limbach, P. A., P. F. Crain and J. A. McCloskey. Summary: the modified nucleotides of RNA. *Nucleic Acids Res.* 22, 2183-2196 (1994).

Malkiewicz, A. and E. Sochacka 1983 The protected derivatives of 5-methylaminomethyl-2-thiouridine and 5-carbomethoxymethyl-2-thiouridine as components for the oligonucleotide synthesis. Tetrahedron Letters 24, 5387-5390.

Murphy F V 4th, Ramakrishnan V, Malkiewicz A, Agris P F. *Nat Struct Mol Biol*. (2004) The role of modifications in codon discrimination by tRNA(Lys)UUU. (12):1186-91.

Nobles K N, Yarian C S, Liu G, Guenther R H, Agris P F. (2002) Highly conserved modified nucleosides influence Mg2+-dependent tRNA folding. Nucleic Acids Res. 30:4751-60.

Ogilvie K K, Usman N, Nicoghosian K, Cedergren R J. 1988 Total chemical synthesis of a 77-nucleotide-long RNA sequence having methionine-acceptance activity. Proc Natl Acad Sci USA. 85:5764-8

Phelps S S, Malkiewicz A, Agris P F, Joseph S. *J Mol Biol*. (2004) Modified nucleotides in tRNA(Lys) and tRNA (Val) are important for translocation 338(3):439-44.

PubChem. http://pubchem.ncbi.nlm.nih.gov/2008. Ref Type: Electronic Citation

Ryszard W. Adamiak and Jacek Stawinski, 1977. A highly effective route to N,N'-disubstituted ureas under mild conditions. an application to the synthesis of tRNA anticodon loop fragments containing ureidonucleosides. *Tetrahedron Letters,* 18: 1935-1936.

Schilling-Bartetzko S, Franceschi F, Sternbach H, Nierhaus K H. Apparent association constants of tRNAs for the ribosomal A, P, and E Sites. J Biol Chem. 1992 Mar. 5; 267(7):4693-702.

Schuette J C, Murphy F V 4th, Kelley A C, Weir J R, Giesebrecht J, Connell S R, Loerke J, Mielke T, Zhang W, Penczek P A, Ramakrishnan V, Spahn C M. GTPase activation of elongation factor E F-Tu by the ribosome during decoding. *EMBO J.* 2009 Mar. 18; 28(6):755-65.

Soll, D. and RajBhandary, U. L. tRNA: structure, biosynthesis, and function. ASM Press, c1995.

Stuart J W, Gdaniec Z, Guenther R, Marszalek M, Sochacka E, Malkiewicz A, Agris P F. (2000). Functional anticodon architecture of human tRNALys3 includes disruption of intraloop hydrogen bonding by the naturally occurring amino acid modification, t6A. Biochemistry. 39:13396-404.

Sundaram M, Crain P F, Davis D R. 2000. Synthesis and characterization of the native anticodon domain of *E. coli* tRNA(Lys): simultaneous incorporation of modified nucleosides mnm(5)s(2)U, t(6)A, and pseudouridine using phosphoramidite chemistry. J Org Chem. 65:5609-14.

Thiaville et al. *Molecular Microbiology* 2015 98(6), 1199-1221. Essentiality of threonylcarbamoyladenosine(t6A), a universal, in bacteria.

Tropsha, A, Golbraikh, A. 2007. Predictive QSAR Modeling Workflow, Model Applicability Domains, and Virtual Screening. *Curr. Pharm. Des.* 13: 3494-504

Vendeix FA1, Dziergowska A, Gustilo E M, Graham W D, Sproat B, Malkiewicz A, Agris P F. Anticodon domain modifications contribute order to tRNA for ribosome-mediated codon binding. Biochemistry. 2008 Jun. 10; 47(23):6117-29

Vondenhoff G H, Van Aerschot A. *Eur J Med Chem.* 2011 46(11):5227-36. Aminoacyl-tRNA synthetase inhibitors as potential antibiotics.
von Ahsen U, Green R, Schroeder R, Noller H F. Identification of 2'-hydroxyl groups required for interaction of a tRNA anticodon stem-loop region with the ribosome. RNA. 1997 January; 3(1):49-56.
Ward A, Campoli-Richards D M. *Drugs.* 1986 32(5):425-44. Mupirocin. A review of its antibacterial activity, pharmacokinetic properties and therapeutic use.
Wells B D, Cantor C R. 1980. Ribosome binding by tRNAs with fluorescent labeled 3' termini. *Nucleic Acids Res.* 1980 Jul. 25; 8(14):3229-46.
Xu ZQ1, Flavin M T, Flavin J. *Expert Opin Investig Drugs.* 2014 23(2):163-82. Combating multidrug-resistant Gram-negative bacterial infections.
Yarian C, Townsend H, Czestkowski W, Sochacka E, Malkiewicz A J, Guenther R, Miskiewicz A, Agris P F. *J Biol Chem.* (2002) Accurate translation of the genetic code depends on tRNA modified nucleotides. 277(19):16391-5.
Zhang J. H., Chung T. D. Y., Oldenburg, K. R *J. Biomol. Screen* (1999) A simple statistical parameter for use in the evaluation and validation of high throughput screening assays. 4, 67-73.
Zhang R, Ou H Y, Zhang C T. Nucleic Acids Res. 2004 Jan. 1; 32 (Database issue): D271-2. DEG: a database of essential genes.

Although the foregoing invention has been described in some detail by way of illustration and example for purposes of clarity of understanding, it will be obvious that certain changes and modifications may be practiced within the scope of the appended claims.

The invention claimed is:

1. A method of identifying, by screening, a specific inhibitor of RNA translation in selected spectrum bacteria, comprising:

contacting, in the presence of a test compound, a nucleic acid molecule having the nucleic acid sequence CCUGCUUcmo5UGCACGCAGG-label (SEQ ID No. 5), or UGCUUcmo5UGCACGCAGG-label (SEQ ID No. 17), which nucleic acid molecule is a portion of the tRNA anticodon stem loop associated with Gram negative bacteria that use GCA to code for alanine, wherein the nucleic acid molecule is a single stranded nucleic acid molecule no more than 20 nucleotides in length, with a ribosome or an aminoacyl synthetase capable of binding to the nucleic acid molecule;

incubating under conditions that allow binding of the nucleic acid molecule and the ribosome or aminoacyl synthetase in the absence of the test compound, and detecting the inhibition or promotion of binding of the nucleic acid molecule and the ribosome or aminoacyl synthetase by the test compound, wherein:

a selected spectrum bacteria is a Gram negative bacteria which must use GCA to code for alanine, the inhibition or promotion of binding indicates whether said test compound is useful for inhibiting Gram negative bacterial propagation, the label undergoes a change when it goes from an unbound state in which it is not bound to the ribosome to a bound state in which it is bound to the ribosome or aminoacyl synthetase, the detection step involves detecting the change, if any, in the label, and the lack of a change indicates that the nucleic acid molecule did not bind to the ribosome or aminoacyl synthetase, and the presence of a change indicates that the nucleic acid molecule did bind to the ribosome or aminoacyl synthetase, and the method identifies compounds that selectively inhibit RNA translation in bacteria that use GCA to encode for Ala, but will not inhibit RNA translation in bacteria that use alternative codons for Ala.

2. The method of claim 1, wherein:
a) the nucleic acid molecule is one which forms a complex with alanine and with the ribosome, and
b) the binding between the nucleic acid molecule and the ribosome is specifically related to alanine incorporation into a peptide or protein in targeted bacteria, but not alanine incorporation into bacteria which do not use GCA to code for alanine.

3. The method of claim 1, wherein the label is fluorescein.

4. The method of claim 1, wherein the detection step involves fluorescence polarization.

5. The method of claim 1, wherein the label is detectable, either directly or indirectly, by spectroscopic, photochemical, biochemical, immunochemical, or chemical means.

6. The method of claim 1, wherein the nucleic acid molecule has the sequence CCUGCUUcmo5UGCACGCAGG-Fluorescein (SEQ ID No. 5).

7. The method of claim 6, wherein the label is detectable, either directly or indirectly, by spectroscopic, photochemical, biochemical, immunochemical, or chemical means.

8. The method of claim 1, wherein the label is selected from the group consisting of radioactive isotopes, dyes, fluorescent dyes, fluorophores, electron dense reagents, enzymes and their substrates, biotin-streptavidin, digoxigenin, and hapten.

9. The method of claim 1, wherein the label is an affinity tag.

10. The method of claim 1, wherein the selected spectrum bacteria are selected from the group consisting of *A. baumannii, E. coli, Klebsiella pneumoniae*, and *Pseudomonas aeruginosa*.

* * * * *

SEQUENCE LISTING

```
<160> NUMBER OF SEQ ID NOS: 17

<210> SEQ ID NO 1
<211> LENGTH: 17
<212> TYPE: DNA
<213> ORGANISM: A. baumannii

<400> SEQUENCE: 1
cctgctttgc acgcagg                                                  17

<210> SEQ ID NO 2
<211> LENGTH: 17
<212> TYPE: DNA
<213> ORGANISM: E. coli

<400> SEQUENCE: 2
ctaccttgag gtggtag                                                  17

<210> SEQ ID NO 3
<211> LENGTH: 17
<212> TYPE: DNA
<213> ORGANISM: Klebsiella pneumoniae

<400> SEQUENCE: 3
cacgcctgga aagtgtg                                                  17

<210> SEQ ID NO 4
<211> LENGTH: 17
<212> TYPE: DNA
<213> ORGANISM: Pseudomonas aeruginosa

<400> SEQUENCE: 4
tcgggctcat aacccga                                                  17

<210> SEQ ID NO 5
<211> LENGTH: 18
<212> TYPE: RNA
<213> ORGANISM: Artificial Sequence
<220> FEATURE:
<223> OTHER INFORMATION: synthetic sequence of an anti-codon stem loop
      (ASL) coding for Alanine
<220> FEATURE:
<221> NAME/KEY: misc_feature
<222> LOCATION: (8)..(8)
<223> OTHER INFORMATION: modified base - n is 5-carboxymethoxyuridine
      (cmO5U)

<400> SEQUENCE: 5
```

```
ccugcuungg cacgcagg                                                18
```

<210> SEQ ID NO 6
<211> LENGTH: 18
<212> TYPE: RNA
<213> ORGANISM: Artificial Sequence
<220> FEATURE:
<223> OTHER INFORMATION: Minimal RNA sequence that includes the SO
      sequence, a box sequence, the AUG codon encoding methionine, and
      the triplet codon for Ala used by certain bacteria

<400> SEQUENCE: 6

```
aggagauaau aaauggca                                                18
```

<210> SEQ ID NO 7
<211> LENGTH: 54
<212> TYPE: RNA
<213> ORGANISM: Artificial Sequence
<220> FEATURE:
<223> OTHER INFORMATION: Minimal RNA sequence that includes the SO
      sequence, the box sequence, the AUG sequence encoding methionine,
      and the triplet codon encoding alanine in certain bacteria, with
      additional bases to the left and right of this sequence

<400> SEQUENCE: 7

```
gggcgauaac acucaggaga uaauaaaugg caacagcuga ucaaucgugc aucc        54
```

<210> SEQ ID NO 8
<211> LENGTH: 17
<212> TYPE: RNA
<213> ORGANISM: Artificial Sequence
<220> FEATURE:
<223> OTHER INFORMATION: tRNA sequence for an anti-codon stem loop
      coding for leucine (LEU)
<220> FEATURE:
<221> NAME/KEY: misc_feature
<222> LOCATION: (11)..(11)
<223> OTHER INFORMATION: modified base - N is 1-methyl guanosine (m1G)
<220> FEATURE:
<221> NAME/KEY: misc_feature
<222> LOCATION: (12)..(12)
<223> OTHER INFORMATION: modified base - N is pseudouridine (p)

<400> SEQUENCE: 8

```
cuaccuugag nngguag                                                 17
```

<210> SEQ ID NO 9
<211> LENGTH: 17
<212> TYPE: RNA
<213> ORGANISM: Artificial Sequence
<220> FEATURE:
<223> OTHER INFORMATION: tRNA fragment ASL coding for serine (SER)
<220> FEATURE:
<221> NAME/KEY: misc_feature
<222> LOCATION: (14)..(14)
<223> OTHER INFORMATION: Modified base - n is pseudouridine (p)

<400> SEQUENCE: 9

```
cacgccugga aagngug                                                 17
```

<210> SEQ ID NO 10
<211> LENGTH: 17
<212> TYPE: RNA
<213> ORGANISM: Artificial Sequence
<220> FEATURE:
<223> OTHER INFORMATION: tRNA anti-codon stem loop sequence coding for
      methionine
<220> FEATURE:
<221> NAME/KEY: misc_feature
<222> LOCATION: (6)..(6)

<223> OTHER INFORMATION: Modified base - n is 2'-O-methylcytidine (cm)

<400> SEQUENCE: 10
ucgggnucau aacccga                                                    17

<210> SEQ ID NO 11
<211> LENGTH: 17
<212> TYPE: RNA
<213> ORGANISM: Artificial Sequence
<220> FEATURE:
<223> OTHER INFORMATION: tRNA fragment coding for alanine (ALA)

<400> SEQUENCE: 11
ccugcuuugc acgcagg                                                    17

<210> SEQ ID NO 12
<211> LENGTH: 17
<212> TYPE: RNA
<213> ORGANISM: Artificial Sequence
<220> FEATURE:
<223> OTHER INFORMATION: tRNA fragment coding for leucine

<400> SEQUENCE: 12
cuaccuugag gugguag                                                    17

<210> SEQ ID NO 13
<211> LENGTH: 17
<212> TYPE: RNA
<213> ORGANISM: Artificial Sequence
<220> FEATURE:
<223> OTHER INFORMATION: tRNA fragment coding for serine

<400> SEQUENCE: 13
cacgccugga aagugug                                                    17

<210> SEQ ID NO 14
<211> LENGTH: 17
<212> TYPE: RNA
<213> ORGANISM: Artificial Sequence
<220> FEATURE:
<223> OTHER INFORMATION: tRNA fragment coding for methionine

<400> SEQUENCE: 14
ucgggcucau aacccga                                                    17

<210> SEQ ID NO 15
<211> LENGTH: 17
<212> TYPE: RNA
<213> ORGANISM: Artificial Sequence
<220> FEATURE:
<223> OTHER INFORMATION: Totally synthetic oligomer

<400> SEQUENCE: 15
ucgggcucau aacccga                                                    17

<210> SEQ ID NO 16
<211> LENGTH: 17
<212> TYPE: RNA
<213> ORGANISM: Artificial Sequence
<220> FEATURE:
<223> OTHER INFORMATION: Totally artificial sequence as shown in Figure
      4B
<220> FEATURE:
<221> NAME/KEY: misc_feature
<222> LOCATION: (6)..(6)
<223> OTHER INFORMATION: Modified base - n is 2-thiocytidine (s2C)
<220> FEATURE:

```
<221> NAME/KEY: misc_feature
<222> LOCATION: (8)..(8)
<223> OTHER INFORMATION: Modified base - n is
      5-carboxymethylaminomethyluridine (cmnm5U)
<220> FEATURE:
<221> NAME/KEY: misc_feature
<222> LOCATION: (11)..(11)
<223> OTHER INFORMATION: Modified base - n is
      N-((9-beta-D-ribofuranosylpurine-6-yl)-carbamoyl)threonine (t6A)

<400> SEQUENCE: 16
auggcnuncu nagccau                                                   17

<210> SEQ ID NO 17
<211> LENGTH: 16
<212> TYPE: RNA
<213> ORGANISM: Artificial Sequence
<220> FEATURE:
<223> OTHER INFORMATION: Sequence shown in Sequence ID No. 5, but
      without the initial two cytidines
<220> FEATURE:
<221> NAME/KEY: misc_feature
<222> LOCATION: (6)..(6)
<223> OTHER INFORMATION: Modified base - n is 5-carboxymethoxyuridine
      (cmO5U)

<400> SEQUENCE: 17
ugcuunggca cgcagg                                                    16
```